US012760365B2

(12) United States Patent
Barroso et al.

(10) Patent No.: US 12,760,365 B2
(45) Date of Patent: Oct. 13, 2026

(54) CLINICAL AND MOLECULAR PROGNOSTIC MARKERS FOR LIVER TRANSPLANTATION

(71) Applicant: OPHIOMICS—INVESTIGAÇÃO E DESENVOLVIMENTO EM BIOTECNOLOGIA, SA, Lisbon (PT)

(72) Inventors: Eduardo Barroso, Lisbon (PT); Hugo Pinto Marques, Lisbon (PT); José Pereira Leal, Lisbon (PT); Joana Cardoso Vaz, Lisbon (PT)

( * ) Notice: Subject to any disclaimer, the term of this patent is extended or adjusted under 35 U.S.C. 154(b) by 1191 days.

(21) Appl. No.: 17/712,201

(22) Filed: Apr. 4, 2022

(65) Prior Publication Data

US 2022/0228218 A1 Jul. 21, 2022

Related U.S. Application Data

(63) Continuation-in-part of application No. PCT/EP2020/077757, filed on Oct. 2, 2020.

(30) Foreign Application Priority Data

Oct. 2, 2019 (EP) .................................... 19201218

(51) Int. Cl.
*C12Q 1/6883* (2018.01)

(52) U.S. Cl.
CPC ...... *C12Q 1/6883* (2013.01); *C12Q 2600/118* (2013.01); *C12Q 2600/158* (2013.01)

(58) Field of Classification Search
CPC ............ C12Q 1/6883; C12Q 2600/118; C12Q 2600/158; C12Q 1/6886
See application file for complete search history.

(56) References Cited

U.S. PATENT DOCUMENTS

| | | | |
|---|---|---|---|
| 2013/0344482 | A1 | 12/2013 | Shin |
| 2015/0147761 | A1 | 5/2015 | Meyer |

FOREIGN PATENT DOCUMENTS

| | | |
|---|---|---|
| CN | 101326290 | 12/2008 |
| CN | 106290874 | 1/2017 |
| CN | 107180154 | 9/2017 |
| EP | 2157524 | 2/2010 |
| WO | 2017207545 | 12/2017 |

OTHER PUBLICATIONS

Mas (Mol Med 2006 12(4-6) 97-104).*
Zheng (Oncotarget, 2017, vol. 8, pp. 52321-52332).*
Lee (Gastroenterology, 2004, 127:S51-S55).*
Zhong-Bo Han et al: "Up-regulation of microRNA-155 promotes cancer cell invasion and predicts poor survival of hepatocellular carcinoma following liver transplantation", Journal of Cancer Research and Clinical Oncology, Springer, Berlin, DE, vol. 138, No. I, Nov. 10, 2011 (Nov. 10, 2011), pp. 153-161, XP019995722, ISSN: 1432-1335, DOI: 10.1007/S00432-011-1076-Z.
Seow Chong Lee: "Prognostic biomarkers for prediction of recurrence of hepatocellular carcinoma: Current status and future prospects", World Journal of Gastroenterology, vol. 20, No. 12,2014, p. 3112, XP055750710, CN ISSN: 1007-9327, DOI: 10.3748/wjg.v20.i12.3112.
Wang Li-Ying et al: "Advances in predicting the prognosis of hepatocellular carcinoma recipients after liver transplantation", Science B: International Biomedicine & Biotechnology, Zheijiang University Press, CN, vol. 19, No. 7, Jul. 10, 2018 (Jul. 10, 2018), pp. 497-504, XP036543809, ISSN: 1673-1581, DOI: 10.1631/JZUS.B1700156.
Ming-Chun Lai et al: "Long non-coding RNA MALAT-1 overexpression predicts tumor recurrence of hepatocellular carcinoma after liver transplantation", Medical Oncology, Springer-Verlag, New York, vol. 29, No. 3, Jun. 16, 2011 (Jun. 16, 2011), pp. 1810-1816, XP035102286, ISSN: 1559-131X, DOI: 10.1007/S12032-011-0004-Z.
Po-Chung Kuo et al: "Clusterin expression in nontumor tissue in patients with resectable hepatocellular carcinoma related with postresectional survival :", Journal of the Chinese Medical Association, vol. 82, No. 12, Sep. 17, 2019 (Sep. 17, 2019), pp. 929-934, XP055750888, HK ISSN: 1726-4901, DOI: 10.1097/JCMA.0000000000000195.
Ying Fu et al: "DNA methylation-mediated silencing of matricellular protein dermatopontin promotes hepatocellular carcinoma metastasis by [alpha]3[beta]1 integrin-Rho GTPase signaling", Oncotarget, vol. 5, No. 16, Aug. 30, 2014 (Aug. 30, 2014), pp. 6701-6715, XP055750877, United States ISSN: 1949-2553, DOI: 10. 18632/oncotarget.2239.

* cited by examiner

*Primary Examiner* — Sarae L Bausch
(74) *Attorney, Agent, or Firm* — JMB Davis Ben-David

(57) ABSTRACT

The invention relates to a method for predicting the outcome of a liver transplantation for treatment of hepatocellular carcinoma (HCC), or to a for assigning a HCC patient to receive liver transplantation, comprising the step of determining the expression level of an indicator gene selected from dermatopontin, clusterin, calpain small subunit 1, F-box and WD repeat containing protein 7 and Sprouty RTK signalling antagonist 2 in a liver sample obtained from a patient suffering from HCC, and comparing the indicator gene expression level to the expression level of an internal control gene, which combined with the variable Total Tumor Volume using a linear support vector machine algorithm predicts positive prognosis of liver transplant recipients.

10 Claims, 14 Drawing Sheets

Specification includes a Sequence Listing.

Variable value is indicator gene expression (ΔCt)

CLINICAL AND MOLECULAR PROGNOSTIC MARKERS FOR LIVER TRANSPLANTATION

CROSS-REFERENCE TO RELATED APPLICATIONS

This is a Continuation-in-Part of International Patent Application No. PCT/EP2020/077757, filed on Oct. 2, 2020, which claims priority to European Patent Application No. 19201218.5, filed Oct. 2, 2019. The contents of the foregoing applications are incorporated herein by reference in their entirety.

FIELD

The present invention relates to a method for prognosis, or to determine the likelihood of positive outcome, of a patient scheduled or considered to receive a liver transplantation in the course of treatment of hepatocellular carcinoma. An integrated application of both clinical and molecular markers allows an improved selection of potential candidates for liver transplantation compared to current criteria for selection of patients. Its application will contribute to an improved selection of patients for liver transplantation necessitated by hepatocellular carcinoma.

BACKGROUND

Hepatocellular carcinoma (HCC) is a highly prevalent disease that significantly impacts mortality and quality of life. It is important to understand its multifactorial etiology and complex etiopathogenesis to inform patient stratification for current therapies or to design personalized medicine optimised for a patient's genome. Liver transplantation (LT) is the best treatment for HCC in cirrhosis, yet organ availability is limited due to the high likelihood of poor outcomes for this disease. Furthermore, it is believed that the expansion of current criteria will lead to a greater demand for transplants, leading in turn to longer waiting times on pre-transplant lists, increasing withdrawal rates, and worsening intention-to-treat outcomes. Even when organs are available, the benefit of LT has to be balanced against the risk for the donor.

An optimised selection of HCC patients is therefore imperative. The stringency of current clinical morphological models, namely the Milan Criteria (MC), may exclude excellent candidates, for example, patients with advanced, yet "benign" tumours that were discovered late in the course of the disease. Conversely, the MC may not exclude patients with early HCC characterised by more aggressive forms of tumour behaviour. The identification of the best candidates for liver transplantation in patients with HCC in the setting of cirrhosis can potentially increase the number of candidates for LT, and therefore influence the demand on the donor pool.

Molecular biomarkers can provide relevant information about the biological behaviour of tumours. At the present moment, however, there are no available consensual prognostic biomarkers that allow proper selection of patients for transplantation, as very few studies have addressed HCC molecular biomarkers in patients. The inventors propose that it is important to focus on the genes, or gene signatures that affect prognosis, as criteria based on morphology of tumours can only partially discriminate patients with good/bad prognosis. Of these, genes that are expressed in HCC patients with a good prognosis (i.e., those where upregulation results in a good outcome) may supplement currently accepted criteria to select a subgroup of patients with a high likelihood of benefitting from LT. Of course, there is also an important role for negative predictor genes, as they allow identification of patients where disease is likely to recur.

Dermatopontin (DPT)

DPT, also known as TRAMP (Tyrosine-rich acidic matrix protein) (Gene ID GC01M168664), is an extracellular matrix protein with possible functions in cell-matrix interactions and matrix assembly. The protein is found in various tissues, and is thought to be expressed in mesenchymal cells (fibroblasts and myofibroblasts) and macrophages. This molecule is critical for extracellular matrix assembly, cell adhesion and wound healing. It also accelerates collagen fibrillogenesis, and modifies the behaviour of TGF-beta through interaction with decorin in the microenvironment of the extracellular matrix in vivo. DPT inhibits the formation of decorin TGF-beta1 complex and may increase the cellular response to TGF-beta and enhance its biological activity. Furthermore, it has been identified as a downstream target of vitamin D receptor. Vitamin D receptor, in turn, mediates signalling downstream of 1,25-dihydroxy-vitamin $D_3$ to exert an anti-proliferative effect on HCC. DPT is correlated with cellular adhesion and tumour invasiveness. Strong expression of DPT has been associated with metastases suppression in oral cancer and giant cell tumour of bone. Down-regulation of DPT is related to carcinogenesis and progression of HCC via possible interaction with TGF-beta1 and other potential mechanisms. The DPT expression level is significantly lower in HCC tissues than in healthy liver.

Calpain Small Subunit 1 (CAPNS1)

Calpains, a family of proteases, are involved in cell migration and invasion by altering the architecture of cell adhesion molecules and cytoskeletal components, or by interfering in intracellular signalling pathways. Its regulatory subunits CAPNS1 and CAPN4 may play an important role in calpain activity. Knockdown of CAPNS1 in malignant endothelial cells may reduce their ability to spread, while CAPNS1 up-regulation is correlated with increased tumour size, number and alpha-fetoprotein (AFP) levels after HCC resection in animals.

Clusterin (CLU)

The protein encoded by the CLU gene chaperone (CLU, Gene ID GC08M027596) that is both cytosolic and secreted. CLU in complex with EIF3I activates the Akt pathway, which in turn promotes metastasis of HCC cells.

F-Box and WD Repeat Containing Protein 7 (FBXW7, Gene ID GC04M152321).

The gene F-box and WD repeat domain containing 7 (FBXW7), also known as Sel10, hCDC4 or hAgo, encodes a member of the F-box protein family, which functions as the substrate recognition component of the SCF E3 ubiquitin ligase. FBXW7 protein is a critical tumor suppressor and one of the most commonly deregulated ubiquitin-proteasome system proteins in human cancer. FBXW7 controls proteasome-mediated degradation of oncoproteins such as cyclin E, c-Myc, Mcl-1, mTOR, Jun, Notch and AURKA. Mutations in this gene are detected in ovarian and breast cancer cell lines, implicating the gene's potential role in the pathogenesis of human cancers. In vitro studies have shown that FBXW7 can be used as a prognostic marker in hepatocellular carcinoma and it was shown that lower FBXW7 expression levels are associated with worse survival of HCC patients. Thus FBXW7 has an important role in HCC progression, namely it inhibits HCC cell migration and invasion through the Notch1 signaling pathway.

Sprouty RTK Signalling Antagonist 2 (SPRY2, Gene ID GC13M080335)

The *Drosophila* Spry (dSPRY) gene family comprising the four homologs SPRY1 to 4, is thought to participate in a negative feedback loop of the RAF/MEK/ERK pathway associated with HCC carcinogenesis. SPRY2, in particular, antagonizes growth factor-mediated cell proliferation, migration and differentiation by modulating receptor tyrosine kinase (RTK) signalling and suppressing the RAF/MEK/ERK pathway. This protein is an important modulator of vital pathways implicated in cancer development, such as angiogenesis, cell growth, invasion, migration and cytokinesis.

SUMMARY

Based on the above mentioned state of the art, the objective of the present invention is to provide molecular markers which help accurately select from amongst all HHC patients the best candidates for LT. The molecular markers should be able to predict the behaviour and aggressiveness of the tumours. This objective is attained by the claims of the present specification, with further advantageous embodiments provided in the specification as a whole.

The inventors refine clinical criteria for the selection of cirrhotic HCC patients for LT and evaluated the role of selected biomarkers in the population. The inventors validated the role of current clinical markers to specifically determine the best candidates for LT in the subgroup of patients beyond the current clinical gold standard of the Milan criteria, integrating both clinical and molecular features to accurately address the biology of the tumours.

A set of possible candidate genes was identified using clinical data in public repositories, a systematic review on the subject of molecular prognostic biomarkers for HCC, and in-house clinical data available to the inventors. The inventors identified single gene alterations with prognostic value, and combined them into predictive multivariate signatures. The systematic review was able to identify genes related to progression of HCC that were assumed to deliver prognostic information after LT, consequently contributing to patient selection for LT.

The inventors demonstrate herein that DPT, CLU, CAPNS1, FBXW7 and SPRY2 exhibit differential expression in patients with and without recurrence of HHC following LT. Furthermore, DPT and CLU effectively discriminate, alone or in combination, a subgroup of patients with no recurrence of HCC after LT, and thus a positive prognosis.

BRIEF DESCRIPTION OF THE FIGURES

FIG. 8A, patients beyond MC; FIG. 8B, patients with TTV>115 $cm^3$; FIG. 8C, patients with microvascular invasion; FIG. 8D, patients with poorly differentiated tumours.

BRIEF DESCRIPTION OF THE DESCRIBED SEQUENCES

Figure 1:
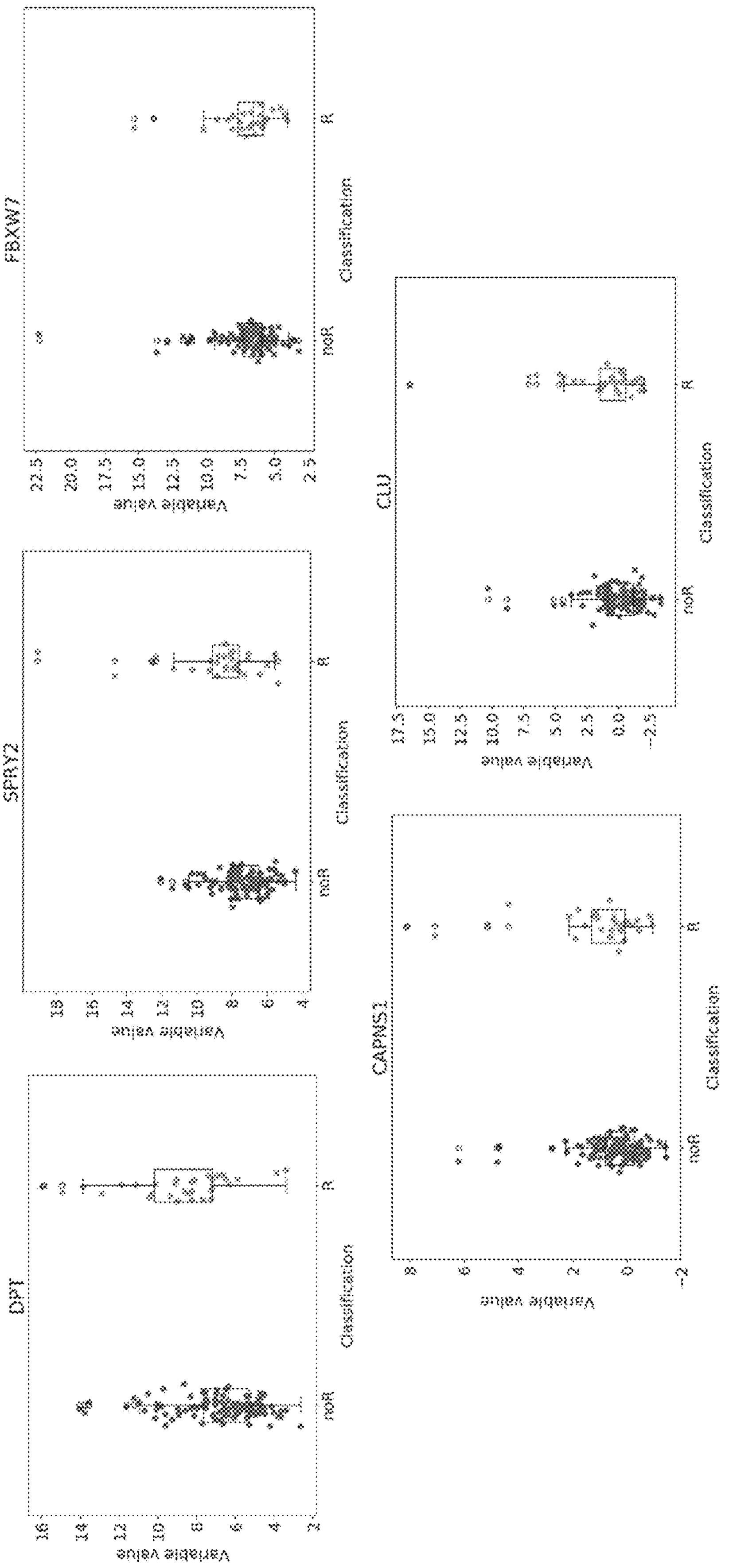
FIG. 1 shows the RT-qPCR results for differential expression of selected genes according to recurrence in the validation set. relapse (R: left) versus no relapse (noR: right). Wilcoxon (Mann-Whitney) test (confidence level=0.95).

The nucleic and/or amino acid sequences provided herewith are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named 95083_391_1_seqlist, created Apr. 4, 2022, about 7 KB, which is incorporated by reference herein.

DETAILED DESCRIPTION

The terms gene expression or expression, or alternatively the term gene product, may refer to either of, or both of, the processes—and products thereof—of generation of nucleic acids (RNA) or the generation of a peptide or polypeptide, also referred to transcription and translation, respectively, or any of the intermediate processes that regulate the processing of genetic information to yield polypeptide products. The term gene expression may also be applied to the transcription and processing of a RNA gene product, for example a regulatory RNA or a structural (e.g. ribosomal) RNA. If an expressed polynucleotide is derived from genomic DNA, expression may include splicing of the mRNA in a eukaryotic cell. Expression may be assayed both on the level of transcription and translation, in other words mRNA and/or protein product.

The term good prognosis in the context of the invention refers to no recurrence of HHC disease in the five years following LT. Good prognosis is measured in the examples by its direct association with patient survival, hence overall survival, or disease-free survival are largely equivalent.

The term support vector machine, SVM, linear kernel SVM or SVM algorithm in the context of the invention refer to a supervised machine learning model that is able to classify data and/or perform regression analysis. It is sometimes referred to as a support vector network, and in the context of the invention, is used as a form of binary linear classifying algorithm. In the context of the invention, the algorithm uses a training step, wherein a sample of patient data is associated with a set of variables, including, but not limited to, a gene expression level, or tumor volume measurement, to build a model that assigns the samples to one category or another, for example, survival, or no survival at five years.

In one aspect, the invention relates to a method for predicting the outcome of a liver transplantation for treatment of HCC. In an alternative of this aspect, the invention relates to a method of treatment of HCC by liver transplantation. In another alternative aspect, the invention relates to a method for stratifying HCC patients into different groups which are more or less likely to benefit from receiving a liver transplantation, in other words, who will exhibit longer overall survival after LT, without recurrence of disease.

The method according to this aspect of the invention comprises a determination step, wherein the expression level (particularly an mRNA level) of a genetic biomarker, or indicator gene (also herein: indicator gene expression level) in a liver sample is obtained from a patient suffering from HCC, wherein said indicator gene is selected from the list comprising a. dermatopontin
b. clusterin
c. calpain small subunit 1
d. F-box and WD repeat containing protein 7
e. Sprouty RTK signalling antagonist 2.

In certain embodiments, the indicator gene is CLU or DPT

In an alternative of this first aspect of the invention, the method for predicting the outcome of a liver transplantation for treatment of hepatocellular carcinoma (HCC), comprises:

in a determination step, determining the expression level of each of a group of indicator genes comprising CLU and DPT in a liver sample obtained from a patient suffering from HCC, in a classification step, assigning a patient a good prognosis as an outcome for liver transplantation based on the expression level of the indicator genes.

In certain embodiments, the group of indicator genes further comprises at least one of:

calpain small subunit 1
F-box and WD repeat containing protein 7
Sprouty RTK signalling antagonist 2.

In certain embodiments, an overexpression of any of the indicator genes is indicative of a good prognosis.

In certain embodiments, an overexpression of the expression of DPT and/or CLU is indicative of a good prognosis.

In certain embodiments, the indicator gene is overexpressed in relation to a threshold. In alternative embodiments, the indicator gene expression level is compared to control samples, selected from representative patients for each disease outcome subset.

In certain embodiments, the indicator gene expression level is determined by use of a quantitative polymerase chain reaction (PCR) sensitive to level of mRNA encoding an indicator gene present in the sample. Specific primers which amplify a region of the indicator gene of interest specified by the invention are provided in Table 6, and may be of particular use to determine the expression level of the indicator genes according to the method provided by the invention. Global RNA sequencing is an alternative methodology that can generate gene expression levels for use according to the invention, The indicator gene expression level may be compared to an internal control gene, particularly to the expression level of a house-keeping gene. In particular embodiments, it is compared to the expression level of ribosomal protein L13A (RPL13A) (Gene ID 23521). Other possibilities include other house-keeping genes, such as GADPH, and/or TBP, or a combination of genes.

In certain embodiments, the indicator gene expression level is determined by PCR. The indicator gene expression value relative to the threshold is determined as a difference of a threshold cycle number of said indicator gene and a threshold cycle number of an internal control gene. The threshold cycle number is a PCR cycle number at which a product [said indicator gene and said internal control gene are] is detected.

In certain embodiments, the following calculation is used to generate a value which reflects the expression level of an indicator gene:

$$\text{Amount of target}=\Delta Ct$$

$$\Delta Ct\ (R)=Ct\ (DPT \text{ in } R)-Ct\ (\text{reference gene in } R)$$

$$\Delta Ct\ (\text{non}R)=Ct\ (DPT \text{ in non}R)-Ct\ (\text{reference gene in non}R)$$

wherein R is a sample with disease recurrence and nonR is a sample without disease recurrence.

In certain embodiments, the indicator gene is DPT and the threshold is a difference in gene expression, or ΔCt, higher than 7.

In certain embodiments, the indicator gene is CLU and the threshold is a difference in gene expression, or ΔCt, higher than −0.54.

In certain embodiments, the difference of the threshold cycle number of the indicator gene, aboce which the gene is said to be overexpressed is:

A DPT expression level ΔCt value which is higher than 7 for DPT, and a CLU expression level ΔCt value which is higher than −0.54.

The threshold values provided here are examples of ΔCt values that may be useful to classify gene expression levels according to the invention. They reflect the gene's expression in reference to a house keeping gene. A gene expression level with a positive value is expressed more than the house-keeping reference gene, while a negative expression value indicates that the gene is expressed less than the house-keeping reference gene. Overexpression of an indicator genes is defined as expression over a ΔCt threshold which separates patients with poor prognosis, from patients with a good prognosis.

In certain embodiments, the overexpression of DPT together with the determination of total tumour volume of 115 $cm^3$ are indicative of a good prognosis.

In certain embodiments, the overexpression of CLU, together with the determination of total tumour volume of 115 $cm^3$ are indicative of a good prognosis.

In certain embodiments multiple patient factors, or variables are used to predict patient outcome, for example, the expression level of CLU, DPT and tumour volume. In particular embodiments of this aspect of the invention, expression level of predictive indicator genes CLU and DPT over the specified thresholds indicates a good prognosis. In related embodiments, indicator gene expression and the additional non-genetic variable of HHC tumour volume 115 $cm^3$ is indicative of good prognosis.

In certain embodiments, the expression level of the indicator gene or genes in a patient sample, and/or a tumour volume measurement is incorporated into an algorithm to provide a value reflecting the likelihood of disease recurrence, particularly wherein the algorithm is a support vector machine algorithm, more particularly, wherein the algorithm is a linear kernel support vector machine algorithm.

In certain embodiments, the indicator gene expression levels, and tumour size variable are used in a predictive algorithm, particularly a machine learning algorithm, more particularly a linear kernel support vector machine (SVM) learning algorithm, which classifies the patient into subsets in which a good prognosis, particularly for the next five years following LT, is likely, or not likely.

The data presented in the examples classified over-expression of CLU in a Ct range in this cohort from 27,36 to 40,5 and for DPT from 33,49 to 35,69. Expressed as a change in Ct compared to a control (also known as delta, or ΔCt), −0.54 was determined to be a useful threshold of CLU overexpression. Likewise, a ΔCt threshold of 7 was identified as useful threshold of DPT expression in patient samples. A tumour volume of, or smaller than 115 $cm^3$ was also found to indicate good prognosis. The value of tumour volume refers to the total of all tumours comprised within the liver of the patient; useful methods which may be used to define the tumour volume may be selected from computerised tomography, and magnetic resonance imaging.

Thresholds such as those specified in this aspect of the invention may be of particular use to binarize patient values, to aid classification of patient outcomes. The data presented in example 5 demonstrates useful thresholds for CLU, DPT, and tumour volume. Samples with expression levels or volume below this are assigned a 0, and those with measurements above the threshold are assigned a score of 1. Incorporating multivariate data in a binarized format from a cohort of patients into a SVM algorithm is demonstrated in the examples to create a classification system wherein the resulting score indicates patient outcome following LT.

In certain embodiments, the determination step comprises determining the expression of DPT and the expression of a gene selected from CLU, CAPNS1, FBXW7 and SPRY2, particularly the expression of DPT and CLU.

In certain embodiments, over-expression of CLU or DPT alone is indicative of a good prognosis. In certain embodiments the predictive classification based on an indicator gene expression level, TTV, or a combination of the two as provided by the invention, is combined with additional prognostic prediction factors, such as evaluation under the Milan criteria. The data in the examples demonstrates that the expression level of CLU can predict disease outcome accurately in a subset of HHC patients classified as outside the Milan criteria.

The Milan criteria, introduced by Mazzaferro in 1996 (Mazzaferro et al., N Engl J Med. 1996 Mar. 14;334(11): 693-9), restricts transplantation in adults with HCC as follows: (1) single tumor diameter less than 5 cm; (2) not more than three foci of tumor, each one not exceeding 3 cm; (3) no angioinvasion; (4) no extrahepatic involvement.

The invention further relates to a system for detecting high expression of liver transplant biomarkers. The system comprises means for determining the expression of DPT and the expression of a gene selected from CLU, CAPNS1, FBXW7 and SPRY2, particularly the expression of DPT and CLU.

In another aspect, the invention encompasses the use of primers for amplification and detection of expression of DPT and CLU, and optionally of additional biomarkers selected from CLU, CAPNS1, FBXW7 and SPRY2, in a kit for analysing biomarkers in order to predict the outcome of a liver transplantation for treatment of HCC.

Furthermore, the invention includes a method of treating a patient who has been previously diagnosed with HHC with a liver transplantation procedure, wherein the patient has been classified as likely to have a good prognosis according to the method as specified in any one of the aspects and embodiments recited above. If the patient is classified as likely to have a good prognosis, then the patient is treated with a liver transplantation procedure according to methods know to the art.

The described methods provide the ability to treat HCC in those patients who are most likely to benefit from a liver transplant procedure by first determining if the patient has a good HCC prognosis, as discussed herein, and then treating only those patients so classified.

EXAMPLES

Example 1: Study of Molecular Prognostic Biomarkers

The inventors analysed the performance of several current selection criteria based on morphologic features, highlighting their possibility to exclude good candidates and to wrongfully include bad candidates. The inventors tested previously identified genes as putative biomarkers for HCC prognosis after transplantation. The genes DPT and CLU were effectively able to discriminate, isolated or in combination, a subgroup of patients with a very low probability of recurrence after LT for HCC.

Example 2: Prognostic Molecular Markers in Hepatocellular Carcinoma

Studies with biomarkers in liver resection (LR) were included in the analysis as important information can be obtained in cohorts of patients submitted to LR. Contrary to single genes, overlap between signatures is uncommon in the literature and gene signatures are frequently not reproducible. For that reason, the inventors specifically focused on single-gene biomarkers and not gene signatures. In addition, and as many of the biomarkers were not further tested and validated outside the settings of its original studies, their usage in the present work represents, at least, an effort of external validation.

The inventors retrieved the following data: data type (mRNA, miRNA and protein), prognosis information, specific genes involved, good or bad prognostic genes, alteration type (overexpression, downregulation, hyper/hypomethylation, mutation), patient samples and statistics data and author's observations.

Example 3: Pilot Set

This first group was implemented to better trim the biomarkers linked to a better prognosis identified throughout the literature search and also to further reduce the number of putative biomarkers linked to early recurrence. From the initially proposed 20 patients (see example 6, sample collection) and due to difficulties with RNA extraction from the first samples belonging to older cases, 9 additional patients were included in the test set. Samples from 3 patients were not used due to sample inadequacy. Hence, the pilot set consisted of 26 patients (6 patients beyond MC without recurrence; 7 patients beyond MC with recurrence; 7 patients within MC without recurrence; 6 patients within MC with recurrence). After RNA extraction, cDNA was obtained and RT-qPCR was performed. Finally, differential expression of the evaluated genes was correlated with clinical data. Table 1 shows the results of the test set according to recurrence within or beyond MC.

TABLE 1

Results of the gene expression is based on the test set and its relation to a recurrence. P values according to the results from the Mann-Whitney test.

| Inside Milan Criteria | | Outside Milan Criteria | | All Criteria | |
|---|---|---|---|---|---|
| Gene | p value | Gene | p value | Gene | p value |
| CLU | 0.09 | CLU | 0.02 | CLU | 0.01 |
| CAPNS1 | 0.05 | DPT | 0.06 | FBXW7 | 0.07 |
| FBXW7 | 0.04 | SLC16A4 | 0.08 | DPT | 0.14 |
| OSGIN | 0.60 | MUC15 | 0.20 | MUC15 | 0.14 |
| DPT | 0.12 | FBXW7 | 0.22 | SLC16A4 | 0.34 |
| SALL4 | 0.98 | HNF1B | 0.36 | SPRY2 | 0.38 |
| SPRY2 | 0.13 | SALL4 | 0.37 | OSGIN | 0.39 |
| NOTCH1 | 0.47 | CCR6 | 0.40 | CCR6 | 0.40 |
| CD24 | 0.42 | OSGIN | 0.40 | CD24 | 0.51 |
| CCR6 | 0.73 | SPRY2 | 0.47 | HNF1B | 0.51 |
| ADAMTS5 | 0.68 | CD24 | 0.52 | DKK1 | 0.66 |
| HNF1B | 0.18 | DKK1 | 0.67 | NOTCH1 | 0.73 |
| SLC16A4 | 0.83 | NOTCH1 | 0.69 | SALL4 | 0.73 |
| DKK1 | 0.80 | ADAMTS5 | 0.71 | ADAMTS5 | 0.78 |
| EYA4 | 0.99 | CAPNS1 | 0.96 | CAPNS1 | 0.82 |
| MUC15 | 0.79 | EYA4 | 0.97 | EYA4 | 0.94 |

In patients within MC, Clusterin (CLU, p=0.09), CAPNS1 (p=0.05) and FBXW7 (p=0.04) had significant differential expression according to recurrence. In patients outside the MC, Clusterin (p=0.02), Dermatopontin (p=0.06) and SLC16A4 (p=0.08) also had significant differential expression according to recurrence. Clusterin was the best marker to discriminate overall recurrence (p=0.01). The subset of selected biomarkers CAPNS1, DPT, CLU and FBXW7 passing the selection criteria in the pilot study were then applied to the validation set. Additionally, the inventors included SPRY2 for further downstream analysis in the validation set as its p-value was borderline significant (p=0.13) in the group "Within Milan Criteria" of the pilot set, despite not being significant in the other two groups. MUC15, the other gene also presenting a borderline significant p-value (p=0.14) in the group "ALL Criteria" was not included in the group of genes to be tested in validation set. This exclusion was due to its poor performance in the RT-qPCR (Ct too high and frequent sample failure) likely associated with a very low expression level.

Example 4: Validation Set

The complete population of 301 patients submitted to LT for HCC between September 1992 and February 2014 was considered. According to inclusion and exclusion criteria (see example 6, study population), a total of 275 patients with histologically confirmed HCC were identified in this analysis. Of 44 patients who were excluded, 32 had perioperative mortality and 12 had residual and/or extrahepatic disease. Patients previously included in the pilot set (26) were also excluded, as well as patients with less than 5 years after LT (38). The initial study population consisted of 167 patients. In 33 patients (19.7%), sample analysis was not possible due to extensive tumour necrosis (14/167; 8.3%), low quality RNA extraction (12/167; 7.2%) or unavailability of formalin-fixed paraffin-embedded tissue (7/167; 4.2%). Consequently, 20 additional patients with less than 5 years after LT were added, in a total of 154 patients for the validation set. The total number of patients whose samples were analysed for molecular markers was 180. General characteristics of the pilot set (n=26), validation set (n=154) and the overall population (n=180) are outlined in table 2.

As expected, the pilot set exhibited more aggressive tumor characteristics compared to the validation set, as patients within and beyond MC were evenly distributed in this first set. Patients in the pilot set had more frequently vascular invasion, larger size of tumor, increased TTV and a lower percentage of patients within MC. In the overall population, median donor age was 38, which is in line with the high percentage of FAP donors (Patients suffering from Familial Amyloid Polyneuropathy, are treated with a live transplant, while their liver becomes available to treat other patients). VHC was predominant with 46% of patients infected. An important observation is the short waiting time before LT—median of 1 month corresponding to a mean waiting time of 2.2 months (0-18). Median number of tumours was 1 corresponding to a mean of 2.17 (1-11) and size of largest tumour was 2.75 cm (mean of 3.25 cm varying from 0.3 to 20 cm). Only 120 (66.7%) patients were within MC and 154 (85.6%) were within TTV<115 $cm^3$.

TABLE 2

A comparison of demographic and clinical/pathological characteristics of the pilot set, validation set, and overall population. Comparison is only done between the pilot and validation sets.

| | All patients (n = 180) | Pilot set (n = 26) | Validation set (n = 154) | p |
|---|---|---|---|---|
| Donor characteristics | | | | |
| Male gender, n (%) | 108 (60) | 16 (61.5) | 92 (59.7) | 0.86 |
| Donor age, years, median, (IQR) | 38 (34) | 36 (39) | 38 (36) | 0.77 |
| Cold ischemia time (min), median (IQR) | 465 (162) | 460 (224) | 465 (154) | 0.61 |
| Recipient characteristics | | | | |
| Male gender, n (%) | 164 (91.1) | 24 (92.3) | 140 (90.9) | 0.59 |
| Race (Caucasian), n (%) | 161 (95.8) | 25 (96.2) | 136 (95.1) | 1.0 |
| Age, years, median, (IQR) | 55 (11) | 55.5 (12) | 55 (13) | 0.67 |
| MELD score, median (IQR) | 10.5 (5) | 8.9 (2) | 11 (5) | 0.29 |
| Waiting list, days, median (IQR) | 1 (3) | 1 (5.5) | 1 (3) | 0.39 |
| BMI, median (IQR) | 26.4 (5.9) | 25.8 (7.6) | 27.2 (5.9) | 0.48 |
| Ethanol intake, n (%) | 125 (71.8) | 20 (76.9) | 105 (70.9) | 0.53 |
| HBV infection, n (%) | 24 (13.3) | 2 (7.7) | 22 (14.3) | 0.54 |
| HCV infection, n (%) | 83 (46.1) | 13 (50) | 70 (45.5) | 0.67 |
| Tumour-related factors | | | | |
| AFP, median (IQR) | 7.5 (42.4) | 5.9 (43.6) | 7.75 (47.4) | 0.57 |
| Hist. number of tumours, median (IQR) | 1 (1), 1-11 | 1 (7), 1-11 | 1 (1), 1-11 | 0.34 |
| Hist. size of largest tumour, median (IQR) | 2.75 (34.18) | 7 (6.8) | 2.75 (13.5) | 0.01 |
| Microvascular invasion, n (%) | 28 (15.6) | 9 (34.6) | 19 (12.3) | 0.008 |
| Macrovascular invasion, n (%) | 18 (10) | 8 (30.8) | 10 (6.5) | 0.001 |
| Capsule, n (%) | 10 (5.6) | 1 (3.8) | 9 (5.8) | 1.0 |
| Satellite nodules, n (%) | 21 (11.7) | 5 (19.2) | 16 (10.4) | 0.19 |
| Poorly differentiated, n (%) | 27 (15) | 5 (19.2) | 22 (14.3) | 0.55 |
| Preoperative therapy, n (%) | 81 (45) | 13 (50) | 68 (44.2) | 0.58 |
| Within histological Milan Criteria, n (%) | 120 (66.7) | 13 (50) | 107 (69.5) | 0.051 |
| Hist. total tumour volume ($cm^3$), median (IQF | 14.1 (29.3) | 4.2 (98.9) | 14.3 (29.32) | 0.79 |
| Hist. tumour volume ≤115 $cm^3$ | 154 (85.6) | 18 (78.3) | 136 (88.3) | 0.027 |
| Operative data | | | | |
| Domino LT | 87 (48.3) | 16 (61.5) | 71 (46.1) | 0.14 |
| c 3-4, n (%) | 37 (20.6) | 4 (15.4) | 33 (21.4) | 0.48 |
| Retransplantation, n (%) | 8 (4.4) | 0 | 8 (5.2) | 0.61 |
| Survival data | | | | |
| Patients alive, n (%) | 94 (52.2) | 15 (57.7) | 79 (51.3) | 0.55 |
| Recurrence follow up | 44 (24.4) | 13 (50) | 31 (20.1) | 0.001 |
| Median | 66 | 54.5 | 72 | 0.34 |
| Range | 195 | 104 | 195 | |
| IQR | 82 | 71 | 89 | |

IQR: interquartile range;
AFP: alpha-fetoprotein;
MELD: Model of end stage liver disease.

Expression levels of CAPNS1, DPT, CLU, FBXW7, SLC16A4 and SPRY2 were analysed in the validation set. In a large number of samples, SLC16A4 expression was too low to be determined and further analysis of this specific biomarker was abandoned. FIG. 1 shows the differential expression of selected genes according to recurrence using the Wilcoxon (Mann-Whitney) test.

Calpain Small Subunit 1 (CAPNS1)

CAPNS1 was included in the validation set as it exhibited marginal differential expression (p=0.05) for recurrence in patients within Milan Criteria in the pilot set. Accordingly, CAPNS1 expression levels in the tumour tissue differed significantly according to recurrence in the validation set (OR 1.448, C.I. 1.140-1.840, p=0.002). This did not translate, however, in a corresponding significance in the Hazard Ratio, whether regarding DFS (HR 1.073, C.I. 0.978-1.178, p=0.136) or OS (HR 1.014, C.I. 0.913-1.125, p=0.796). A ROC curve was used to determine a cut-off value for recurrence. With an AUC of 0.63, the best cut-off appeared to be a deltaCT value of 0.20, corresponding to a sensitivity of 65% and a specificity of 45%. However, after categorization of this variable, no impact on DFS (p=0.378) or OS (p=0.655) was noted. Although this marker exhibited some association with recurrence, its distribution shows a substantial overlap between recurring and non-recurring patients.

Dermatopontin (DPT)

Figure 2:
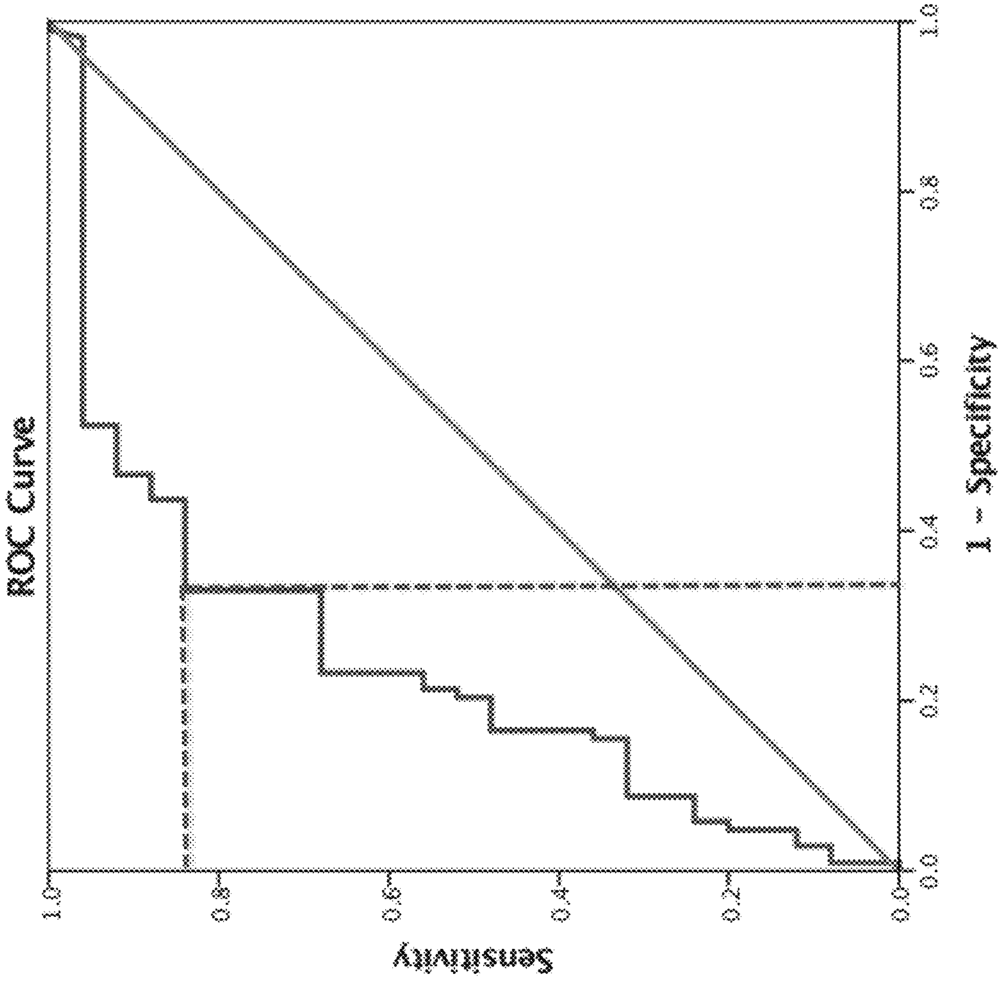
FIG. 2 shows the receiver operating characteristic (ROC) analysis regarding DPT expression and tumour recurrence. Area under curve (AUC) is 0.77. A ΔCt cut-off value of 7, corresponding to 84% sensitivity and 63% specificity, was chosen.

DPT was included in the validation set as its differential expression for recurrence was almost significant in patients beyond Milan Criteria (p=0.06). DPT showed a strong association with recurrence in the validation set (OR 1.283, C.I. 1.103-1.494, p=0.001). Association with DFS (HR 1.048, C.I. 0.977-1.123, p=0.192) or OS (HR 1.036, C.I. 0.961-1.116, p=0.357) was not initially evident. ROC curve analysis revealed an AUC of 0.77 (FIG. 2), allowing a determination of a deltaCT cut-off value of 7, corresponding to 84% sensitivity and 63% specificity. Using this value, a HR value of 0.480 (C.I. 0.295-0.782, p=0.003) was observed for DFS. A HR of 0.503 (C.I. 0.305-0.831, p=0.007) was detected for OR. The risk of recurrence is decreased almost 9-fold with a strong DPT expression (OR 0.116, C.I. 0.037-0.363, p<0.001).

In summary, DPT overexpression indicated a good prognosis after LT. In patients with strong expression of DPT, the risk of recurrence was reduced by 5-fold, disease-free survival increased by 50%, and overall survival increased by 40%. DPT expression was able to discriminate patients with good prognosis after LT amongst poor prognosis groups. It was found an association with microvascular invasion with a possible synergistic effect with CLU expression. This association might be related to its functions in extracellular matrix assembly and cell adhesion, eventually influencing microvascular invasion. This is the first report that associates DPT expression and prognosis after LT for HCC and it is the first time this gene has proven to be an independent predictor of good prognosis.

Sprouty RTK Signalling Antagonist 2 (SPRY2)

This protein is an important modulator of vital pathways implicated in cancer development, such as angiogenesis, cell growth, invasion, migration and cytokinesis. Song et al., (Hepatobiliary & Pancreatic Diseases International 2012; 11(2):177-184) used samples from 240 randomly-selected HCC patients who underwent liver resection to investigate SPRY2 expression on tissue microarrays. Two hundred and seven patients (86.3%) exhibited down-regulation of SPRY2 expression, which correlated to poorer survival (p=0.002) and increased recurrence (p=0.003), acting as an independent predictor of postoperative recurrence in HCC patients (HR=1.47; 95% CI, 1.02-2.08; p=0.037). The inventors' study is the first to correlate overexpression of SPRY2 with increased recurrence in a population of patients submitted to LT for HCC. However, as significant overlap existed between the two groups, the inventors were not able to determine a cut-off value able to effectively discriminate recurring and non-recurring patients. Hence, clinical relevance of SPRY2 remains to be tested in future studies. SPRY2 exhibited some differential expression (p=0.13) for recurrence within Milan Criteria in the pilot set. In the validation set, SPRY2 significantly correlated with recurrence, with an OR of 1.342 (C.I. 1.106-1.628, p=0.003). However, no association was noted on DFS (HR 1.050, C.I. 0.962-1.145, p=0.273) or OS (HR 1.030, C.I. 0.943-1.125, p=0.514). With an AUC of 0.68, we determined the best cut-off to be a deltaCT value of 7.6, corresponding to a sensitivity of 69% and a specificity of 65%. However, still no association was obtained after categorization, either on DFS (HR 1.420, C.I. 0.897-2.248, p=0.134) or in OS (HR 1.305, C.I. 0.814-2.094, p=0.269).

Clusterin

In the pilot set, CLU revealed differential expression for recurrence in patients beyond Milan Criteria (P=0.02) and similarly in the overall set sample (p=0.01). In the validation set, CLU expression did not appear to be associated with recurrence, according to the Wilcoxon test (FIG. 36). However, logistic regression analysis revealed that CLU expression correlated with recurrence in the validation set (OR 1.219, C.I. 1.059-1.403, p=0.006). These results are not incompatible because the Wilcoxon test, though a quite more robust statistical test, is not sensitive to rather subtle differences between groups which, in our case, translate into subtle expression differences between the Recurrence and non-Recurrence groups. No association with DFS (HR 1.073, C.I. 0.978-1.178, p=0.136) or OS (HR 1.014, C.I. 0.913-1.125, p=0.796) was initially found. Using a ROC curve, a OCT cut-off value of −0.54 was determined, corresponding to an AUC of 0.59 (sensitivity of 77%, specificity of 35%). With this cut-off, HR for DFS was 1.568 (C.I. 0.951-2.584, p=0.078) and HR for OS was 1.550 (C.I. 0.926-2.595, p=0.096). Although this association appears to be weak, we considered it enough to be tested in multiple logistic regression and cox regression analysis.

F-Box and WD Repeat Containing Protein 7 (FBXW7)

FBXW7 levels appeared to exhibit differential expression according to recurrence in patients within Milan Criteria in the pilot set (p=0.04). However, this difference was not confirmed in the validation set. Logistic regression revealed an OR of 1.238 (C.I. 0.894-1.052, p=0.545) for recurrence. Cox regression obtained a HR of 1.023 (C.I. 0.929-1.128, p=0.640) for DFS and 1.000 (C.I. 0.900-1.113, p=0.994) for OS.

Example 5: Analysis of the Total Population

The inventors analysed the whole population of 180 patients. Taking into account the results obtained in the validation set, CLU and DPT expression levels, measured by OCT value in relation to the expression of a housekeeping gene in the tumour tissue, were included in this analysis.

Factors associated with recurrence were tested with multiple logistic regressions in this population (table 3). The inventors observe that the number of tumours, microvascular invasion and poor differentiation were independently associated with recurrence, as was histological total tumour volume (TTV). Using DPT expression, the predicted risk of recurrence was reduced more than 5-fold whereas CLU expression predicted a decrease in the risk of recurrence by 61%. However, when both were introduced in the model, only DPT expression remained independently predictive of recurrence (OR 0.178, C.I. 0.063-0.507, P=0.001), but not CLU (OR 0.729, C.I. 0.063-0.507, p=0.554). No statistical interaction between the variables "DPT expression" and "CLU expression" was detected using recurrence as the outcome variable (p=0.402). Both CLU (p=0.94) and DPT (p=0.960) expression had no association with poorly differentiated tumours.

TABLE 3

Multiple logistic regression analysis for recurrence in the overall population (N = 180).

| | Univariable | | | Multivariable analysis | | |
|---|---|---|---|---|---|---|
| | OR | 95% Cl | p | OR | 95% Cl | p |
| Gender | 2.410 | 0.526-11.046 | 0.258 | — | — | — |
| Race | 1.983 | 0.232-16.976 | 0.532 | — | — | — |
| Age >50 | 0.463 | 0.226-0.948 | 0.035 | 0.591 | 0.247-1.416 | 0.238 |
| IMC | 1.021 | 0.945-1.103 | 0.592 | — | — | — |
| Waiting time >120 days | 1.274 | 0.400-4.057 | 0.682 | — | — | — |
| First observation >180 days | 1.333 | 0.634-2.804 | 0.449 | — | — | — |
| Pre-operative therapy | 1.102 | 0.556-2.188 | 0.780 | — | — | — |
| Domino liver transplantation | 1.316 | 0.663-2.609 | 0.432 | — | — | — |
| Morbidity Clavien > II | 0.820 | 0.344-1.955 | 0.654 | — | — | — |
| HBV infection | 1.324 | 0.510-3.439 | 0.564 | — | — | — |

TABLE 3-continued

Multiple logistic regression analysis for recurrence in the overall population (N = 180).

| | Univariable | | | Multivariable analysis | | |
|---|---|---|---|---|---|---|
| | OR | 95% Cl | p | OR | 95% Cl | p |
| HCV infection | 1.090 | 0.552-2.153 | 0.805 | — | — | — |
| Ethanol consumption | 0.722 | 0.341-1.526 | 0.393 | — | — | — |
| MELD | 0.982 | 0.908-1.063 | 0.659 | — | — | — |
| AFP > 400 | 2.028 | 0.195-21.137 | 0.554 | — | — | — |
| Histological number of tumors | 1.265 | 1.114-1.437 | <0.001 | 1.209 | 1.054-1.387 | 0.007 |
| Histological size of tumors | 1.322 | 1.124-1.556 | 0.001 | 1.123 | 0.941-1.340 | 0.197 |
| Capsule | 1.313 | 0.268-6.425 | 0.737 | — | — | — |
| Microvascular invasion | 8.723 | 3.615-21.047 | <0.001 | 4.880 | 1.856-12.829 | 0.001 |
| Macrovascular invasion | 4.706 | 1.725-12.839 | 0.002 | 0.881 | 0.186-4.167 | 0.873 |
| Microsatellite nodules | 5.292 | 2.052-13.645 | 0.001 | 2.879 | 0.979-8.464 | 0.055 |
| Poorly differentiated | 3.025 | 1.289-7.100 | 0.011 | 2.668 | 1.012-7.038 | 0.047 |
| Pre-operative TTV | 1.007 | 1.002-1.013 | 0.013 | 1.005 | 0.998-1.011 | 0.178 |
| Pre-op TTV > 115 | 4.066 | 1.278-12.931 | 0.018 | 0.379 | 0.098-1.470 | 0.161 |
| Pre-operative Milan criteria | 2.564 | 1.150-5.719 | 0.021 | 0.811 | 0.299-2.199 | 0.680 |
| Histological TTV | 1.009 | 1.003-1.015 | 0.002 | 1.006 | 1.001-1.012 | 0.015 |
| HTTV > 115 | 6.000 | 1.929-18.666 | 0.002 | 1.753 | 0.429-7.168 | 0.435 |
| Histological Milan criteria | 4.333 | 2.119-8.862 | <0.001 | 1.747 | 0.696-4.387 | 0.235 |
| DPT > 7 | 0.155 | 0.062-0.387 | <0.001 | 0.177 | 0.064-0.489 | 0.001 |
| CLU > −0.54 | 0.494 | 0.230-1.061 | 0.071 | 0.385 | 0.153-0.971 | 0.043 |

OR: odds ratio; Cl: confidence level.

Strong DPT expression was associated with decreased microvascular invasion (OR 0.370, C.I. 0.140-0.979, p=0.045) whereas CLU expression was not (p=0.173). However, an interaction between DPT and CLU was detected (p=0.033) when microvascular invasion was the outcome variable, which means the occurrence of microvascular invasion in tumours with low or high DPT expression is strongly correlated with the expression of CLU. In this study, 21.2% (14/66) of patients with low DPT expression had microvascular invasion. In this subgroup, if CLU was strongly expressed, the occurrence of microvascular invasion was 4.8% (1/21); if there was concomitant low CLU expression, microvascular invasion was present in 28.9% (13/45) of patients (p=0.027). This interaction has never been detected in the scientific literature and remains to be explained in future studies, suggesting a link between these genes.

TABLE 4

An analysis of multivariable Cox regression for disease-free survival in 180 patients.

| | Univariable analysis | | | Multivariable analysis | | |
|---|---|---|---|---|---|---|
| | HR | 95% Cl | p | HR | 95% Cl | p |
| Gender | 1.677 | 0.733-3.835 | 0.221 | — | — | — |
| Race | 4.900 | 0.682-35.193 | 0.144 | 0.355 | 0.48-2.603 | 0.308 |
| Age >50 | 1.008 | 0.644-1.578 | 0.971 | — | — | — |
| IMC | 1.014 | 0.968-1.062 | 0.554 | — | — | — |
| Waiting time >120 days | 1.433 | 0.692-2.965 | 0.333 | — | — | — |
| First observation >180 days | 1.689 | 1.065-2.678 | 0.026 | 1.139 | 0.564-2.299 | 0.716 |
| Pre-operative therapy | 0.837 | 0.557-1.257 | 0.391 | — | — | — |
| Sequential liver transplantation | 0.989 | 0.660-1.483 | 0.958 | — | — | — |
| Morbidity Clavien > II | .944 | 0.575-1.548 | 0.819 | — | — | — |
| HBV infection | 1.168 | 0.623-2.192 | 0.628 | — | — | — |
| HCV infection | 1.157 | 0.771-1.736 | 0.481 | — | — | — |
| Ethanol consumption | 0.604 | 0.370-0.985 | 0.043 | 1.541 | 0.937-2.534 | 0.089 |
| MELD | 1.009 | 0.977-1.043 | 0.566 | — | — | — |
| AFP > | 1.384 | 0.331-5.777 | 0.656 | — | — | — |
| Histological number of tumors | 1.091 | 1.025-1.162 | 0.007 | 1.068 | 0.997-1.144 | 0.061 |
| Histological size of tumors | 1.065 | 0.999-1.135 | 0.055 | 2.179 | 1.267-3.748 | 0.545 |
| Capsule | 0.779 | 0.341-1.782 | 0.554 | — | — | — |
| Microvascular invasion | 2.468 | 1.522-4.003 | <0.001 | 2.315 | 1.357-3.951 | 0.002 |
| Macrovascular invasion | 2.104 | 1.190-3.723 | 0.011 | 1.184 | 0.546-2.566 | 0.670 |
| Microsatellite nodules | 1.407 | 0.796-2.485 | 0.240 | — | — | — |
| Poorly differentiated | 1.555 | 0.904-2.674 | 0.110 | 1.574 | 0.937-2.534 | 0.134 |
| Pre-operative TTV | 1.001 | 1.000-1.002 | 0.097 | 0.359 | 0.049-2.646 | 0.396 |
| Pre-op TTV > 115 | 0.656 | 0.315-1.364 | 0.259 | — | — | — |
| Pre-operative Milan criteria | 1.054 | 0.615-1.806 | 0.848 | — | — | — |
| Histological TTV | 1.002 | 1.000-1.003 | 0.008 | 1.1001 | 0.999-1.004 | 0.291 |
| HTTV > 115 | 1.754 | 0.876-3.511 | 0.113 | 1.446 | 0.610-3.428 | 0.328 |
| Histological Milan criteria | 1.728 | 1.147-2.605 | 0.009 | 0.203 | 0.692-2.091 | 0.513 |
| DPT > 7 | 0.477 | 0.302-0.754 | 0.002 | 0.507 | 0.310-0.829 | 0.007 |
| CLU > −0.54 | 0.548 | 0.348-0.861 | 0.009 | 0.443 | 0.269-0.730 | 0.001 |

Table 4 shows the results of multivariable cox regression analysis for DFS in the total population. Microvascular invasion was the only factor correlated with a decreased DFS. Strong expression levels of DPT and CLU, on the contrary, acted as positive predictive factors and correlated with an increased survival. Although CLU ceases to be an independent variable when both CLU and DPT are simultaneously introduced in the model (HR 0.600, C.I. 0.351-1.026, p=0.062), no statistical interaction was detected between CLU and DPT (p=0.822).

Dermatopontin (DPT)

Figure 3:
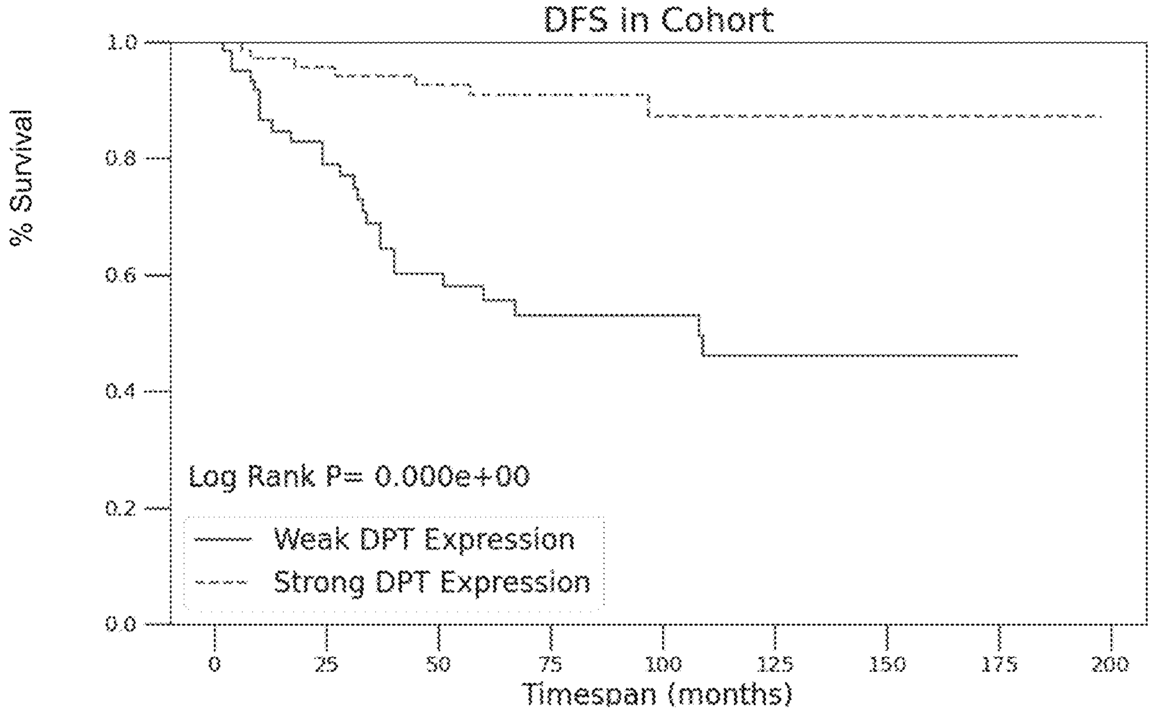
FIG. 3 shows a disease-free survival by DPT expression.
Figure 4A:
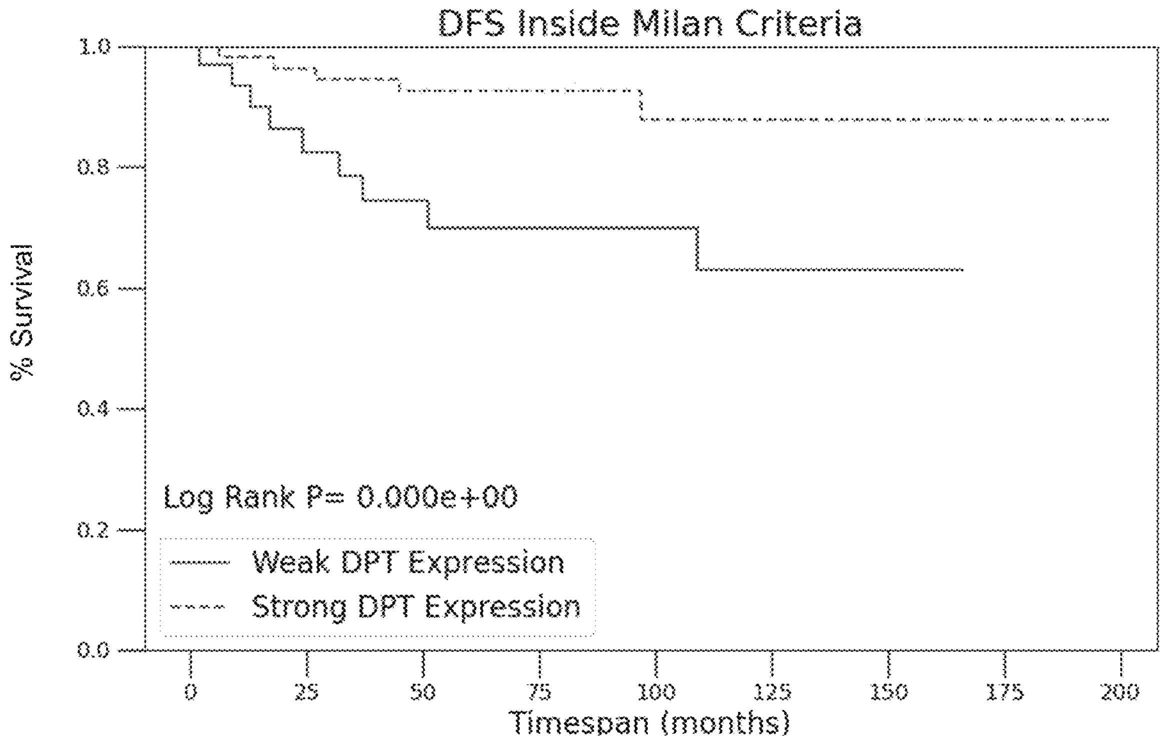
FIGS. 4A-4B show the survival by DPT expression in patients within and beyond Milan Criteria (MC).
Figure 4B:
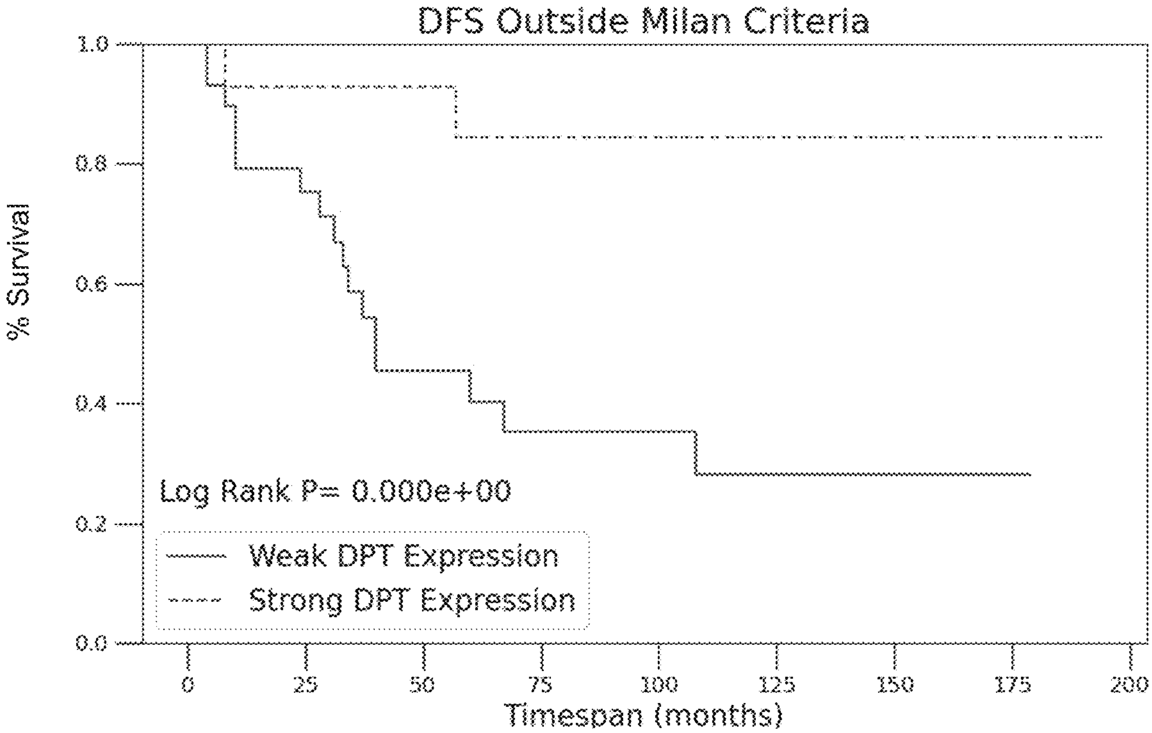
Figure 5A:
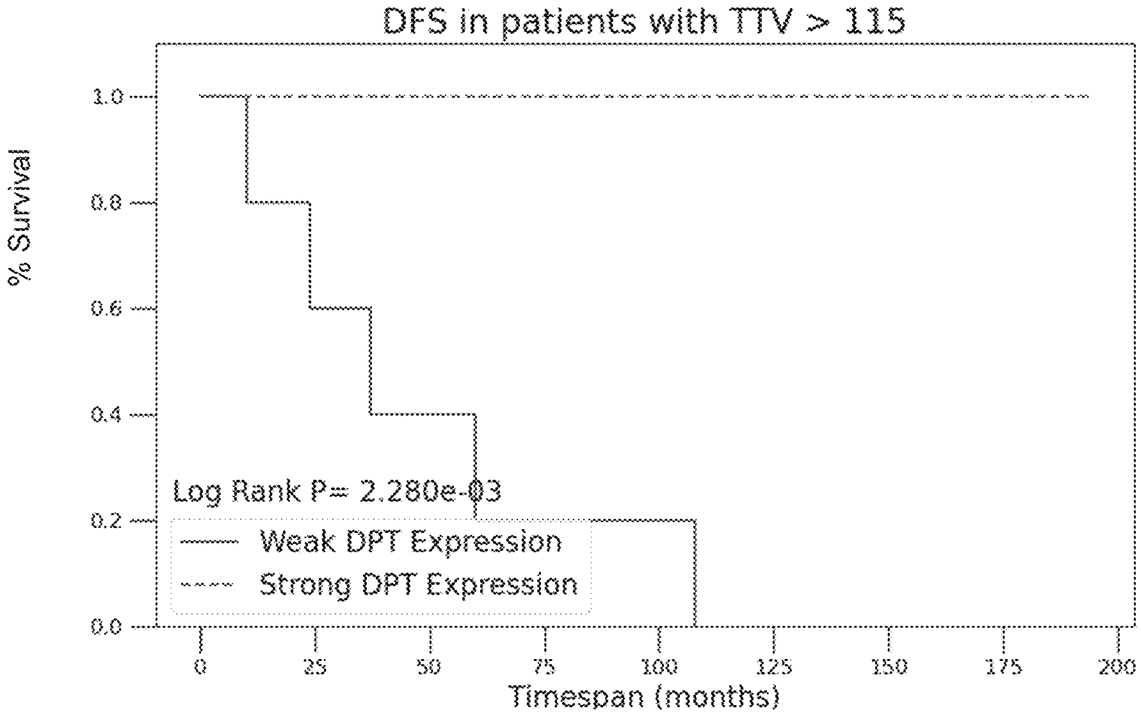
FIGS. 5A-5C show a disease-free survival by DPT expression in patients with a TTV>115 $cm^3$ (FIG. 5A), poor differentiation (FIG. 5B) or microvascular invasion (FIG. 5C).
Figure 5B:
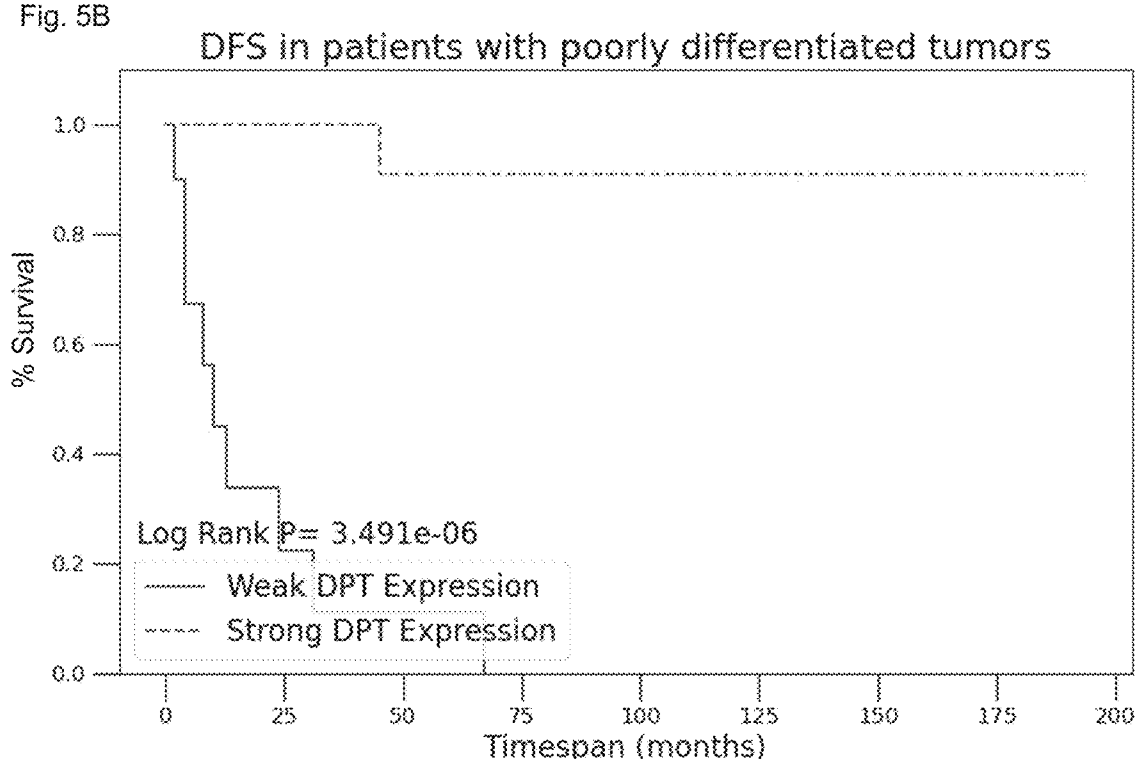
Figure 5C:
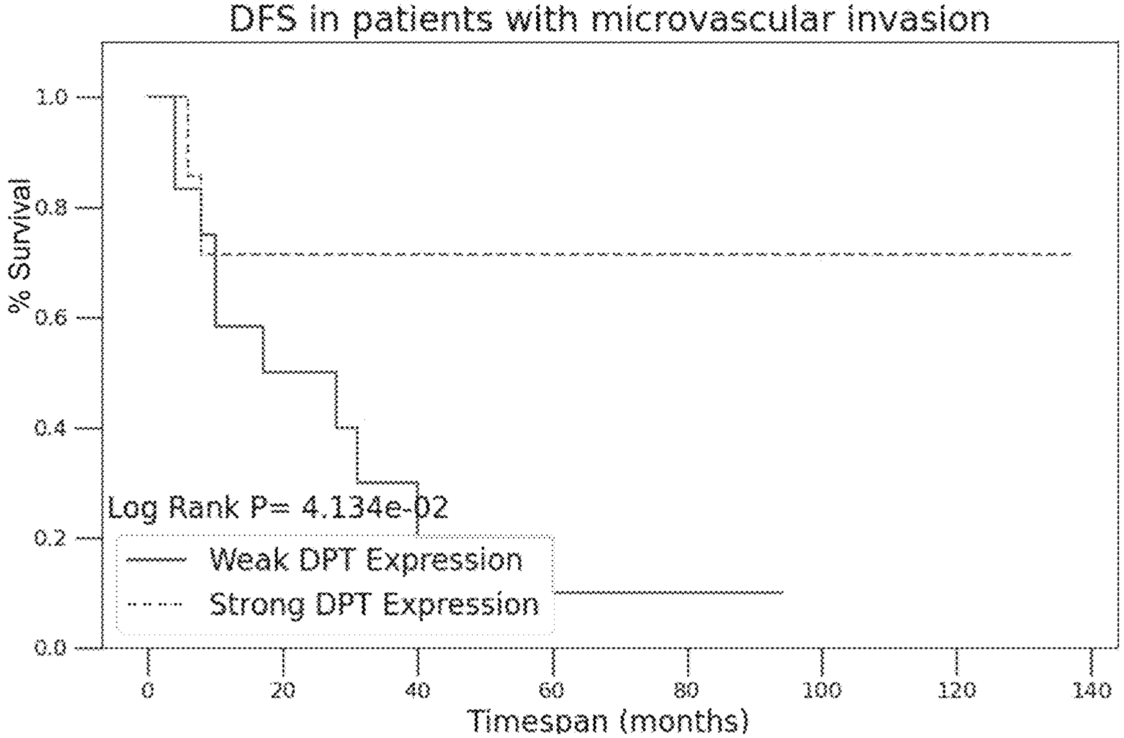
Figure 6:
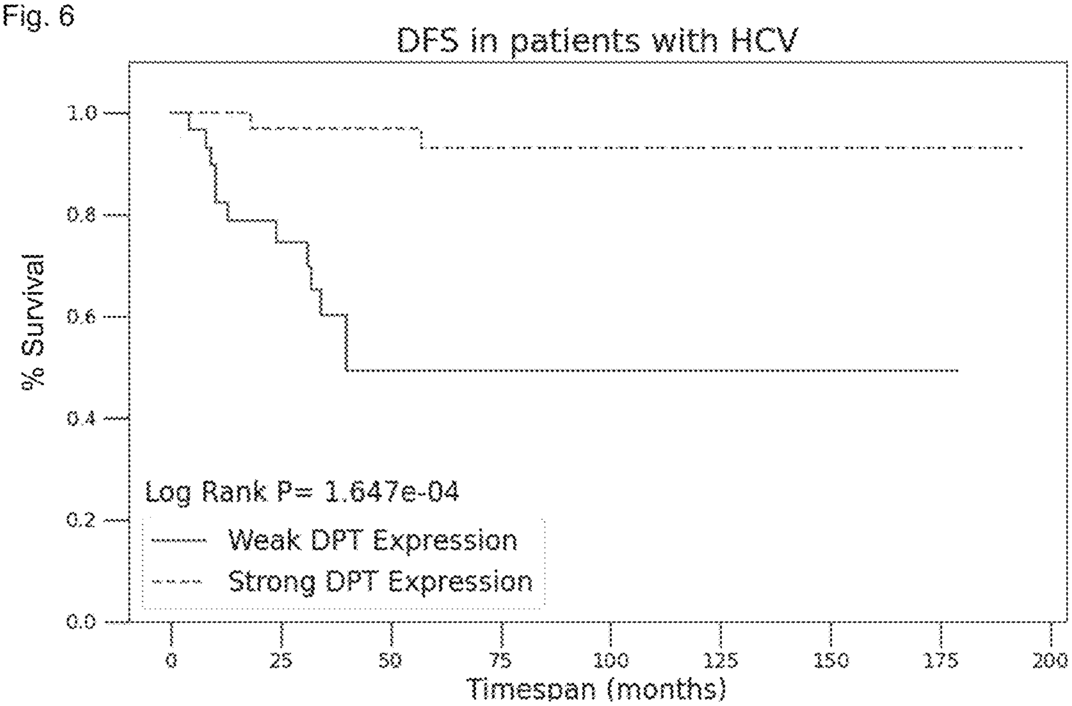
FIG. 6 shows the survival by DPT expression in the subgroup of HCV patients.

The inventors observe DFS according to a strong vs weak DPT expression (FIG. 3). Patients with strong DPT expression, defined as a OCT level above 7, experienced a 70% and a 52.2% DFS at 5 and 10 years respectively. Strong DPT expression was also able to identify a subgroup of patients with better prognosis, even in patients beyond MC (FIG. 4). This was also applied to patients exhibiting other poor prognostic criteria, such as a TTV>115 $cm^3$, the presence of microvascular invasion or poor differentiation (FIGS. 5A, B and C). Finally, the subgroup of HCV patients with strong DPT expression obtained a 5 and 10-years DFS of 79.2% and 58.8% respectively (FIG. 6).

Clusterin (CLU)

CLU expression was analysed in 198 HCC specimens using a tissue microarray (Wang et al., Oncotarget 2015; 6(5); 2903-16). CLU protein was mostly detected in the cytoplasm of tumour cells. Multivariate Cox regression analysis indicated CLU overexpression to be an independent prognostic factor for tumour recurrence after resection (HR 1.628). Also, the same study found that overexpression of CLU significantly promoted invasion of HCC cells in vitro and facilitated distant lung metastasis in vivo, while silencing CLU decreased the invasive ability of HCC cells in vitro and in vivo. CLU overexpression can enhance metastatic potential in prostate, renal cell, gallbladder and breast cancers.

Figure 7:
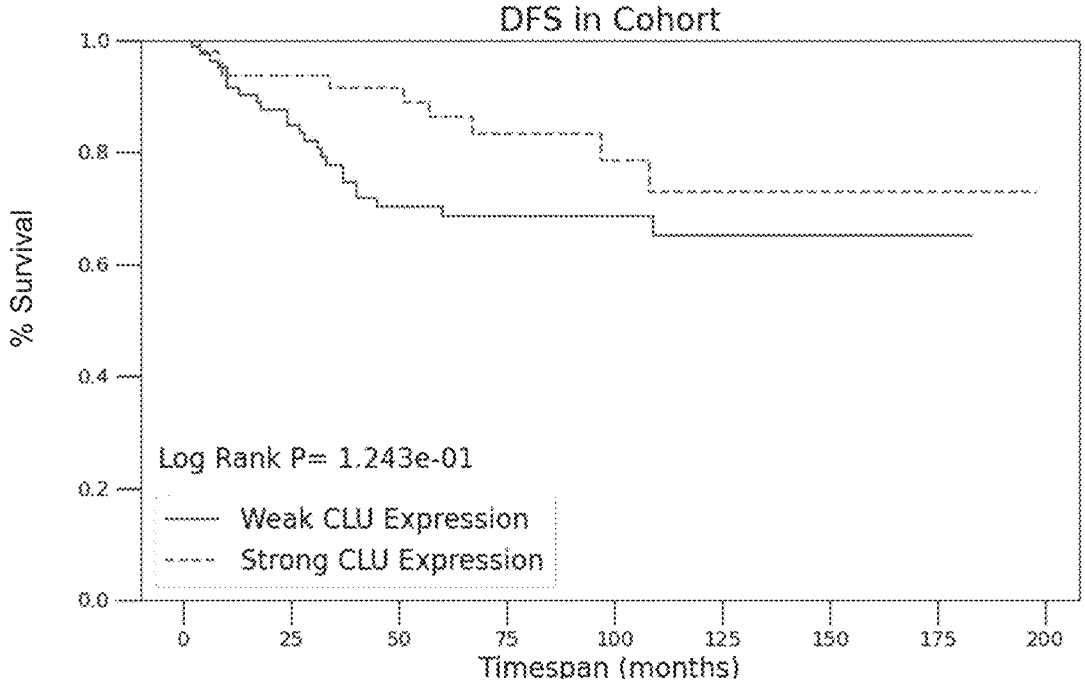
FIG. 7 shows a disease-free survival by CLU expression.
Figure 8A:
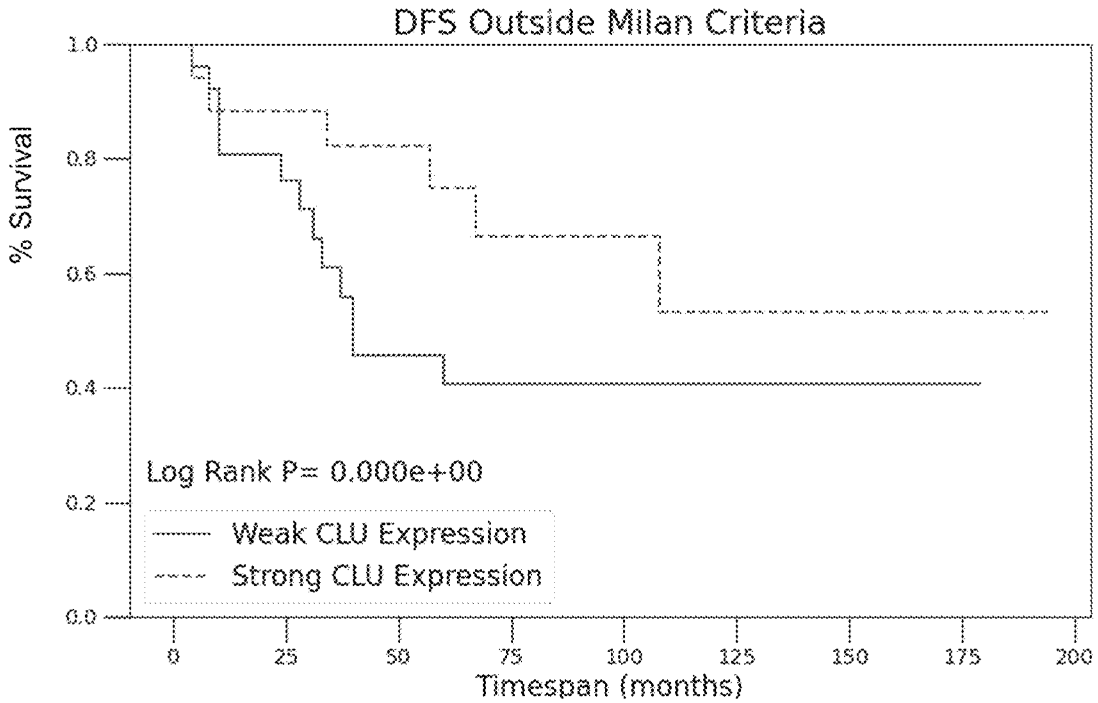
FIGS. 8A-8D show a Disease-free survival according to CLU expression in "poor prognosis" subgroups.
Figure 8B:
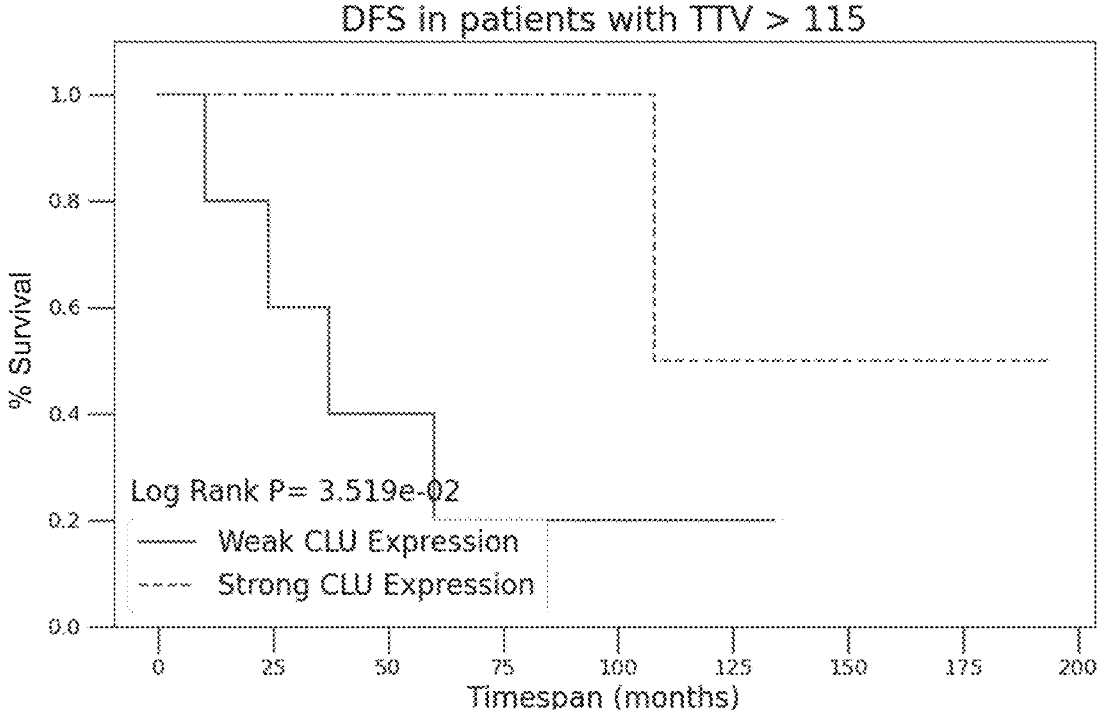
Figure 8C:
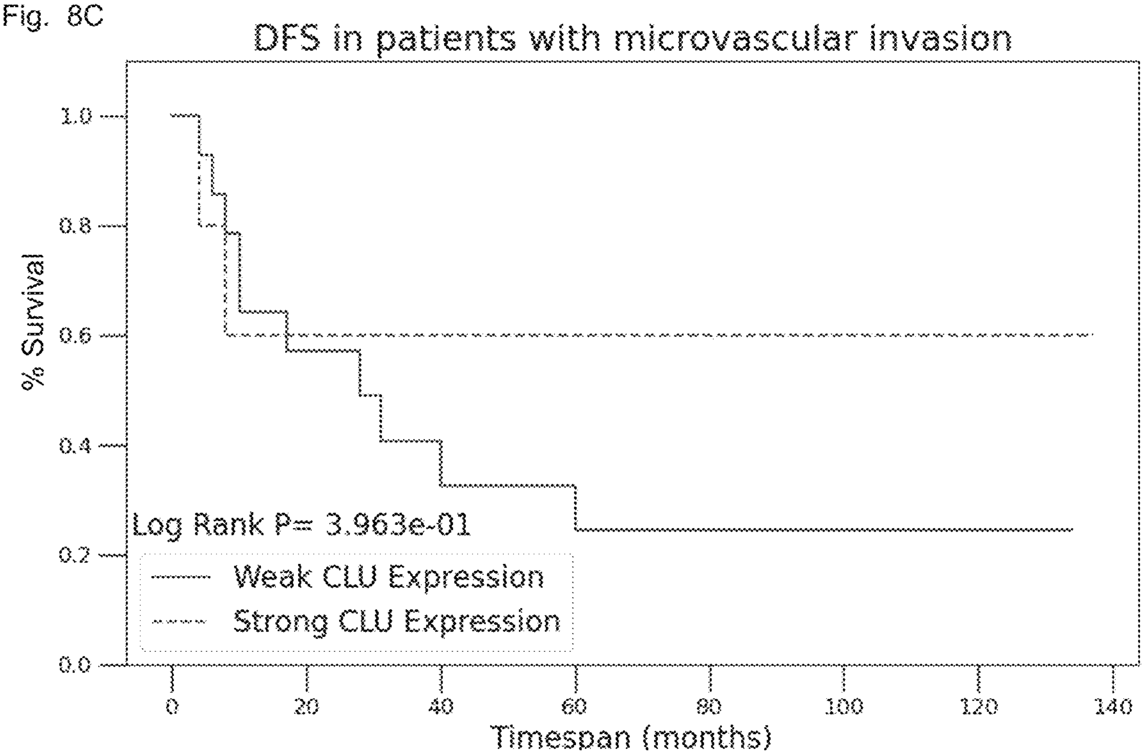
Figure 8D:
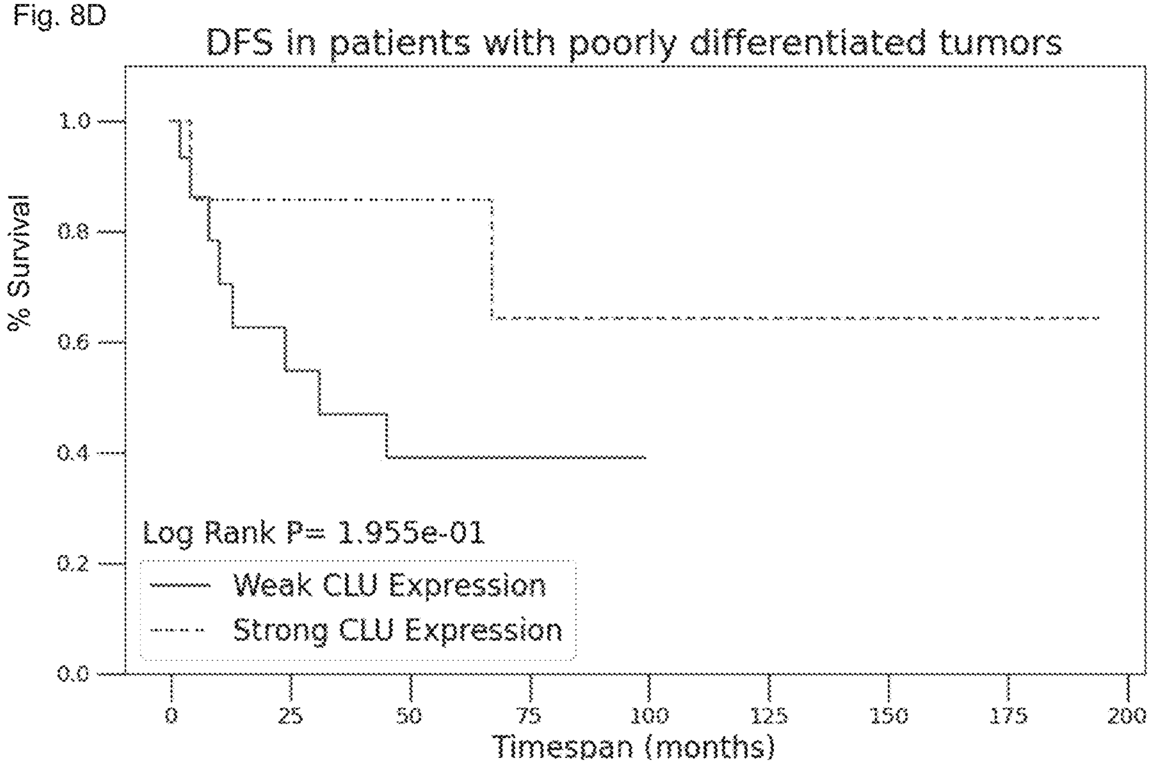
Figure 9:
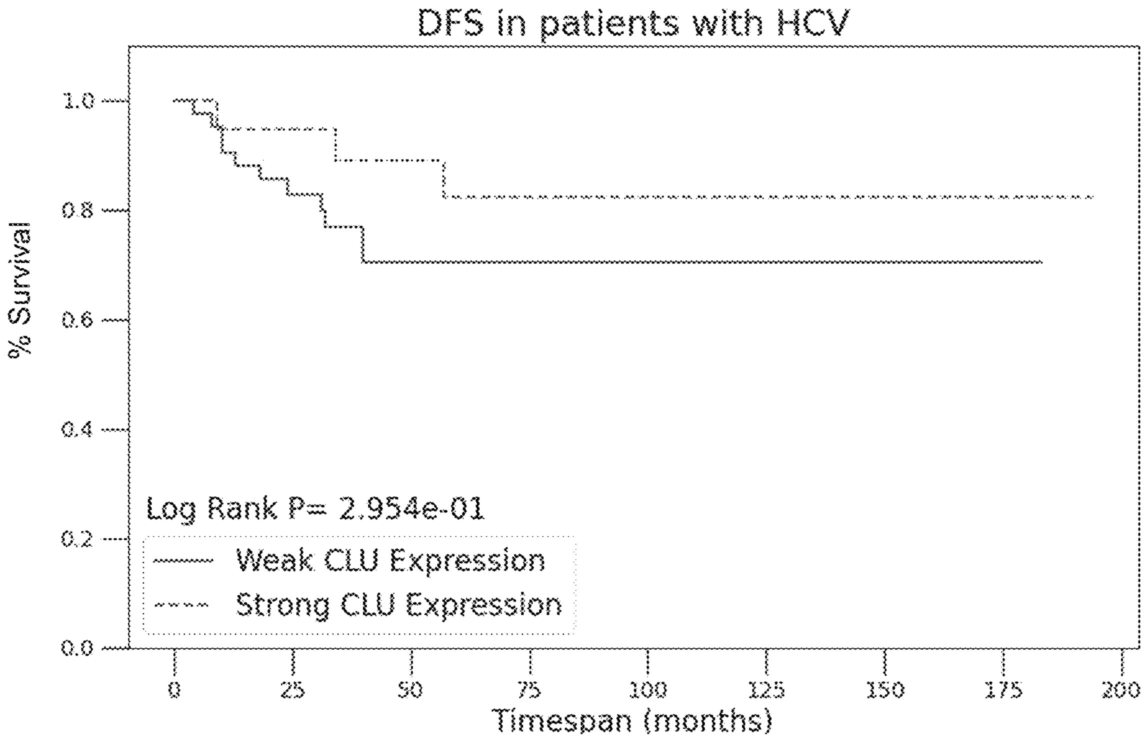
FIG. 9 shows the survival according to CLU expression in Hepatitis C virus (HCV) patients.

In the current cohort, CLU overexpression exhibited association with recurrence and survival and was able to discriminate patients with good prognosis after LT amongst poor prognosis groups. CLU also had an important impact on disease-free survival (DFS) (FIG. 7). Patients with strong CLU expression exhibit a 5 and 10-year survival of 68.9% and 56.1% respectively. Although less pronounced than DPT, CLU expression values alone are able to select patients with better outcome when used within poor prognosis groups, such as patients beyond Milan Criteria (A) or with a TTV>115 $cm^3$ (B). Patients with microvascular invasion (C) or poor differentiation (D) did not have a statistically significant association with survival according to CLU expression, although a clear trend is noted (FIG. 8). The subgroup of HCV patients with strong CLU expression obtained a 5 and 10-years DFS of 74% and 67% respectively (FIG. 9).

TABLE 5

A multivariable Cox regression for overall survival.

| | Univariable analysis | | | Multivariable analysis | | |
|---|---|---|---|---|---|---|
| | HR | 95% Cl | p | HR | 95% Cl | p |
| Gender | 1.831 | 0.742-4.522 | 0.189 | 1.330 | 0.375-4.725 | 0.659 |
| Race | 4.498 | 0.626-32.338 | 0.135 | 1.278 | 0.163-10.009 | 0.815 |
| Age >50 | 0.988 | 0.622-1.572 | 0.960 | — | — | — |
| IMC | 1.012 | 0.964-1.062 | 0.632 | — | — | — |
| Waiting time >120 days | 1.272 | 0.612-2.642 | 0.519 | — | — | — |
| First observation >180 | 1.500 | 0.931-2.417 | 0.095 | 1.623 | 0.982-2.685 | 0.059 |
| Pre-operative therapy | 0.871 | 0.568-1.336 | 0.527 | — | — | — |
| Sequential liver | 0.889 | 0.581-1.362 | 0.589 | — | — | — |
| Morbidity Clavien > II | 0.816 | 0.473-1.406 | 0.463 | — | — | — |
| HBV infection | 0.968 | 0.514-1.823 | 0.919 | — | — | — |
| HCV infection | 1.168 | 0.764-1.784 | 0.473 | — | — | — |
| Ethanol consumption | 1.830 | 1.083-3.091 | 0.024 | 2.156 | 1.236-3.761 | 0.007 |
| MELD | 1.015 | 0.984-1.047 | 0.339 | — | — | — |
| AFP > 400 ng/mL | 0.785 | 0.107-5.763 | 0.812 | — | — | — |
| Histological number of | 1.082 | 1.013-1.156 | 0.018 | 1.029 | 0.944-1.122 | 0.517 |
| Histological size of tumors | 1.048 | 0.975-1.126 | 0.207 | — | — | — |
| Capsule | 0.870 | 0.352-2.152 | 0.764 | — | — | — |
| Microvascular invasion | 2.337 | 1.407-3.883 | 0.001 | 2.536 | 1.446-4.450 | 0.001 |
| Macrovascular invasion | 2.172 | 1.199-3.932 | 0.010 | 1.426 | 0.658-3.090 | 0.369 |
| Microsatellite nodules | 1.543 | 0.868-2.743 | 0.139 | 0.918 | 0.455-1.850 | 0.810 |
| Poorly differentiated | 1.583 | 0.903-2.774 | 0.109 | 1.623 | 0.888-3.143 | 0.112 |
| Pre-operative TTV | 1.000 | 0.999-1.001 | 0.450 | — | — | — |
| Pre-op TTV > 115 | 1.190 | 0.514-2.752 | 0.685 | — | — | — |
| Pre-operative Milan criteria | 1.068 | 0.593-1.921 | 0.827 | — | — | — |
| Histological TTV | 1.001 | 1.000-1.002 | 0.020 | 1.001 | 0.998-1.004 | 0.450 |
| HTTV > 115 | 1.623 | 0.777-3.390 | 0.198 | 1.355 | 0.514-3.572 | 0.539 |
| Histological Milan criteria | 1.677 | 1.091-2.577 | 0.019 | 0.952 | 0.522-1.734 | 0.871 |
| DPT > 7 | 0.539 | 0.335-0.868 | 0.011 | 0.590 | 0.356-0.980 | 0.042 |
| CLU > −0.54 | 0.491 | 0.302-0.799 | 0.004 | 0.490 | 0.279-0.862 | 0.013 |

A multivariable cox regression analysis for overall survival (OS) was also performed. Ethanol consumption and microvascular invasion were independently associated with a decreased OS. While microvascular invasion is a known risk factor, a decrease in OS due to ethanol consumption, without a corresponding decrease in DFS, might be related to associated comorbidities common in ethanolism such as ethanolic myocardiopathy. Strong expression of both DPT and CLU was independently associated with an increased OS (Table 5).

Multivariate Combinations with Predictive Power

Figure 10:
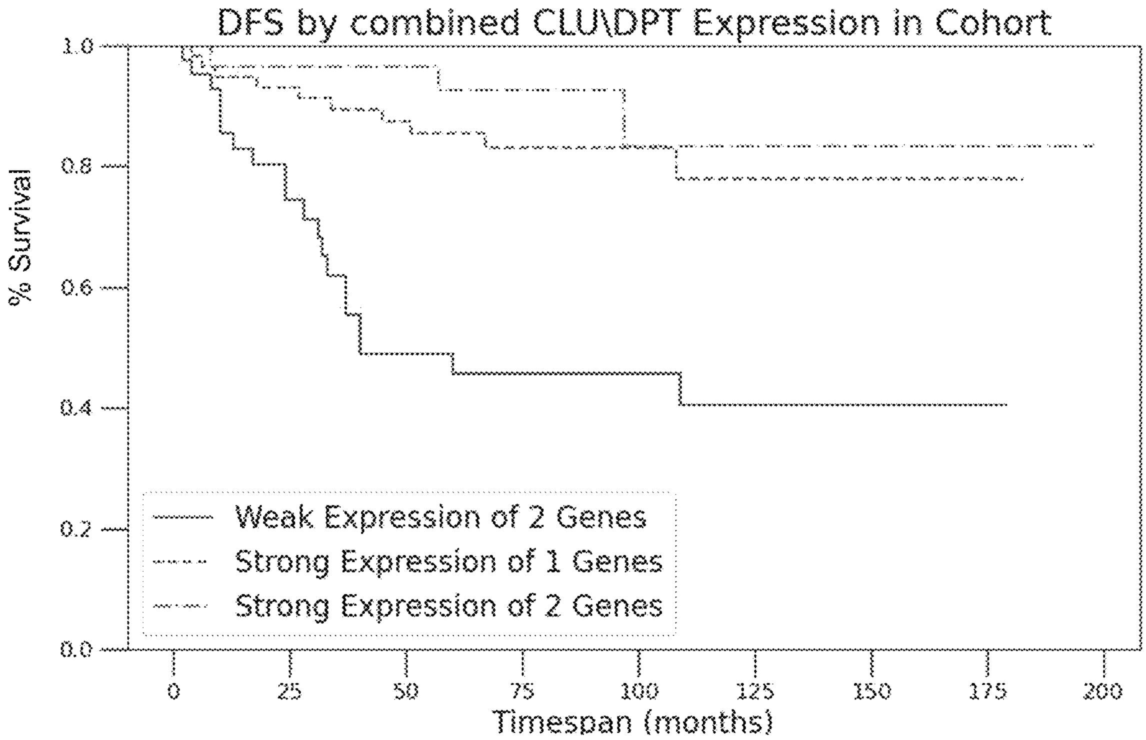
FIG. 10 shows a disease-free survival by composite DPT/CLU score.
Figure 11A:
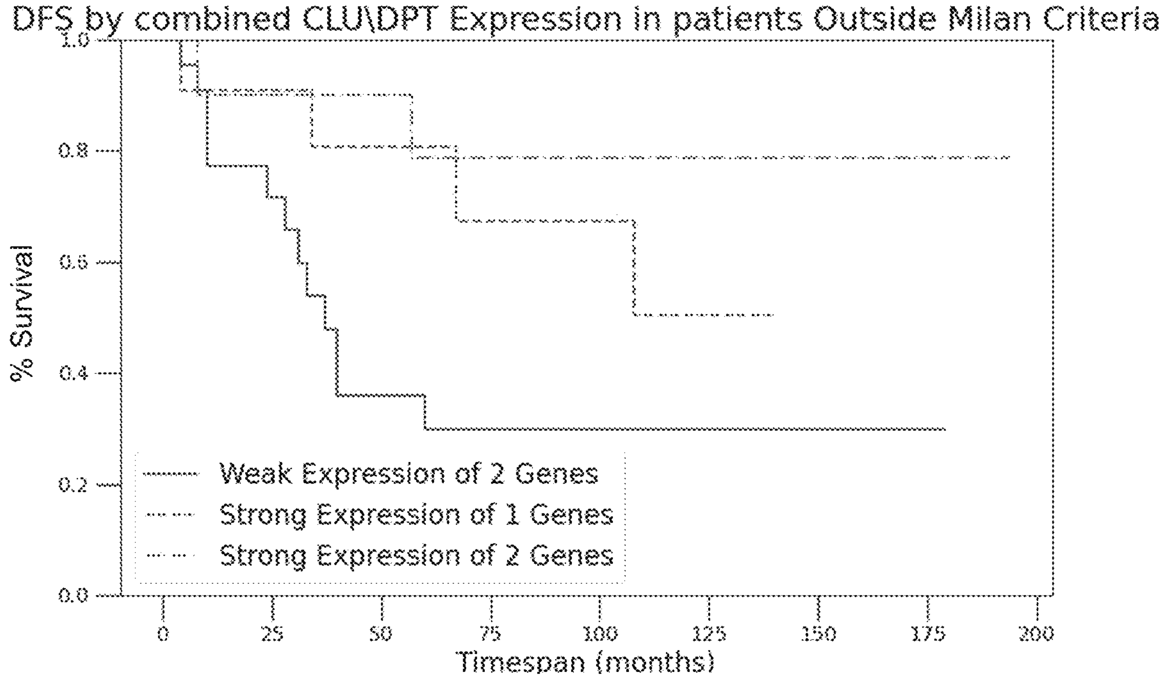
FIGS. 11A-11D show a DFS using composite gene score in patients outside MC (FIG. 11A), with TTV>115 $cm^3$ (FIG. 11B), with poorly differentiated tumours (FIG. 11C), and with microvascular invasion (FIG. 11D).
Figure 11B:
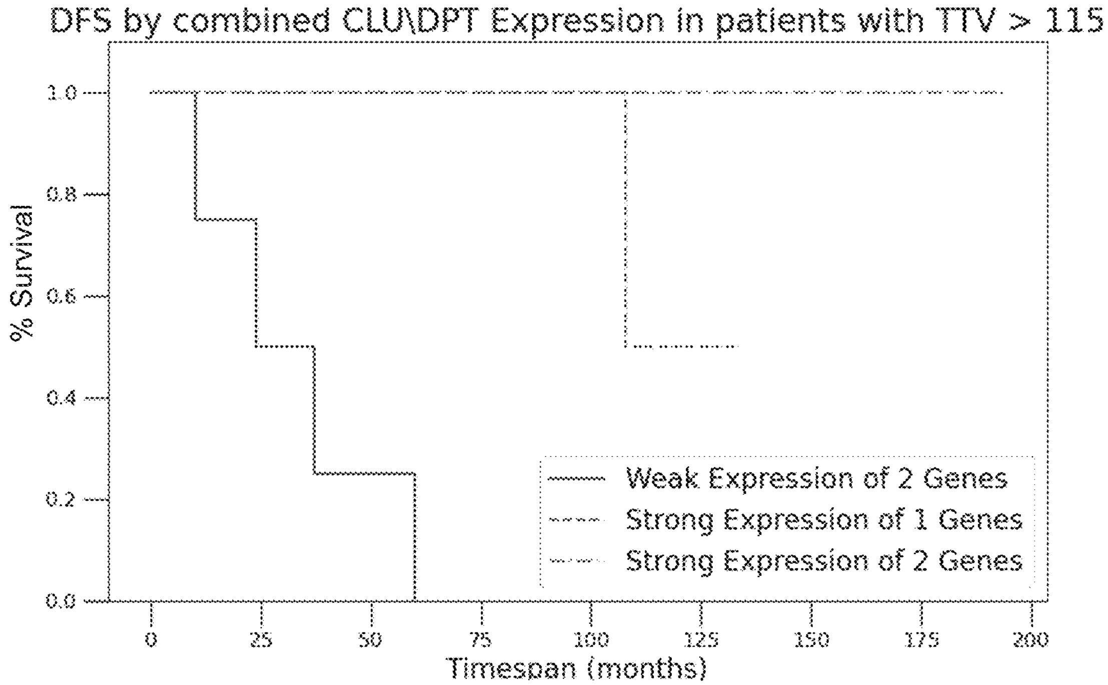
Figure 11C:
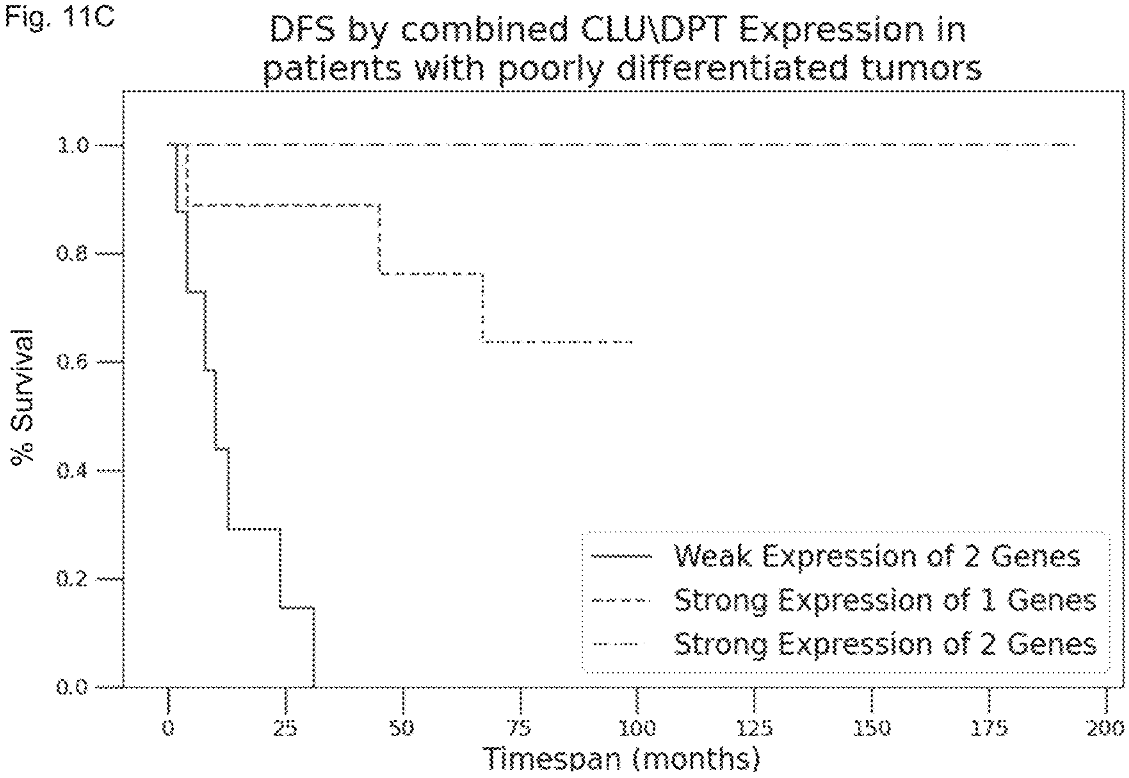
Figure 11D:
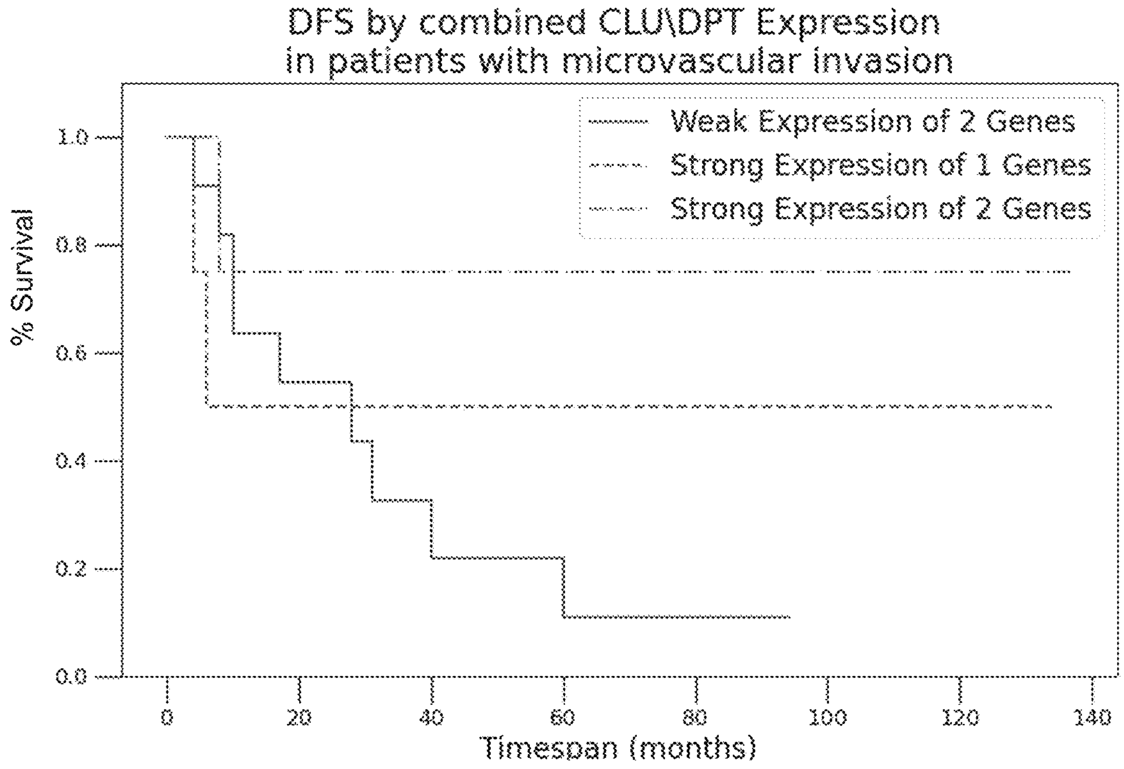
Figure 12:
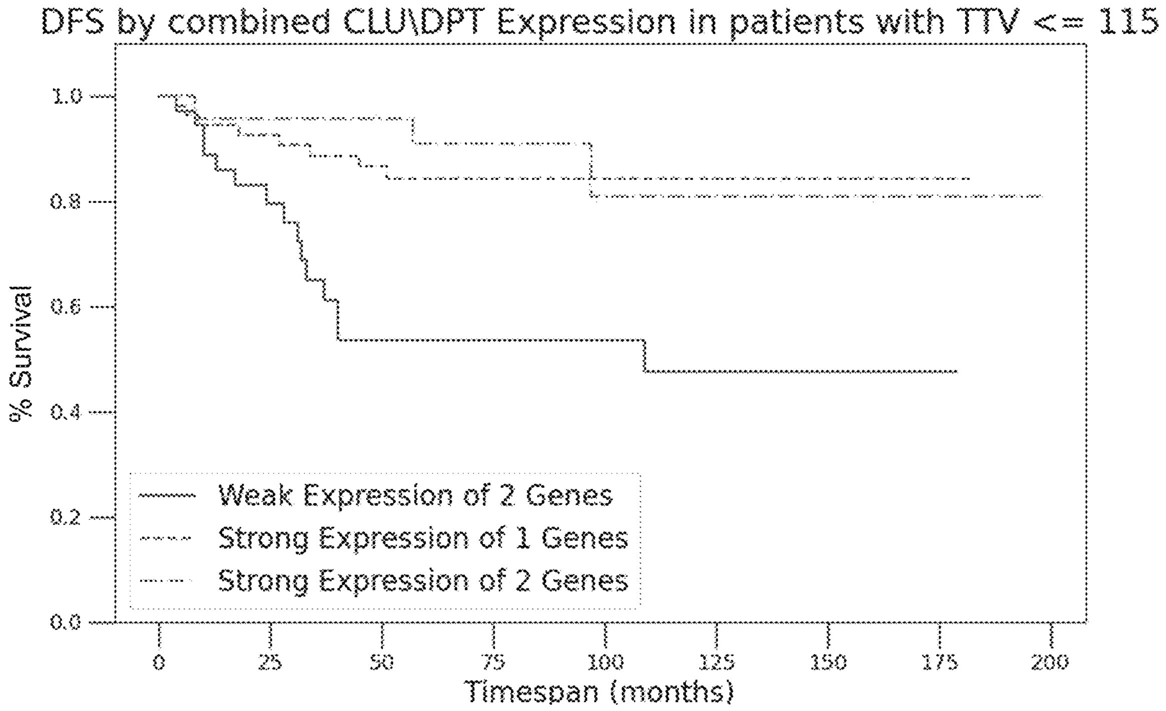
FIG. 12 shows a DFS for composite gene score in patients with TTV≤115 $cm^3$.
Figure 13:
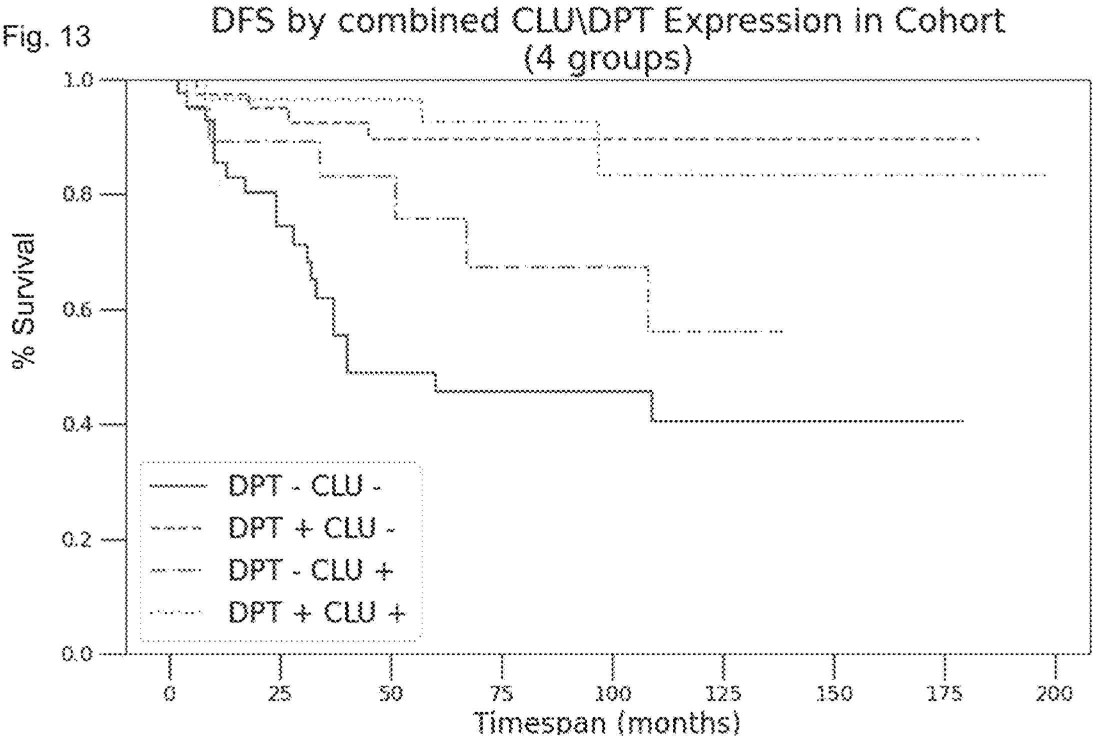
FIG. 13 shows Disease-free survival according to the expression of DPT and CLU separately and combined. DPT expression reveals a better capability to predict long survivors when compared to CLU.

To strengthen the prognostic power of the genes linked to HHC outcome, multigene models combining the predictive power of all genes were developed to investigate a synergistic effect between DPT and CLU. A simple score based on the expression of the two genes combined was used. Since their hazard ratios for DFS were similar, the same points to each gene: 0 points for weak expression of both genes, 1 point for strong expression of 1 gene and 2 points for strong expression of both genes. Strong expression of both genes was linked to 78% and 60% survival at 5 and 10 years respectively, making the gene combination superior to DPT or CLU alone (FIG. 10). This score discriminates good prognosis after LT in patients excluded by the Milan Criteria (FIG. 11A), with TTV>115 $cm^3$ (FIG. 11B) and with poorly differentiated tumours (FIG. 11C). Again, a trend towards increased survival was noted in patients with microvascular invasion, although no statistical significance was reached (FIG. 11D). The results are superior to the ones obtained by each gene separately. FIG. 12 shows the predicted survival using this simple composed gene score combined with TTV≤115 $cm^3$. This combination identifies a group of patients with very good prognosis after LT, a group with intermediate but still acceptable prognosis after LT and a group with poor prognosis after LT. According to the results previously shown for each individual gene, DPT may have a superior predictive power when compared to CLU. Consequently, the combination of these genes was evaluated without the use of a score, to better assess the prognostic power of patients strongly expressing only one of the two genes (FIG. 13).

In a second approach to incorporate multiple genes into a predictive strategy for HCC, the expression level values of the two genes CLU and DPT were used together with TTV, in a Linear kernel support vector machine classification algorithm. To evaluate the performance of the algorithm, a Jackknifing strategy was used i.e. the algorithm is trained using all data points except one, and this one is used to evaluate, the process is then repeated for every datapoint and results were collected. After removing the testing sample, the remaining dataset was subject to a data augmentation (SMOTE) and normalization (unit variance and zero mean) procedure. This was done to attain a balanced training dataset and prevent overfitting to the most prevalent classification, and also ensure that all features are comparable in the classification feature space.

Figure 14:
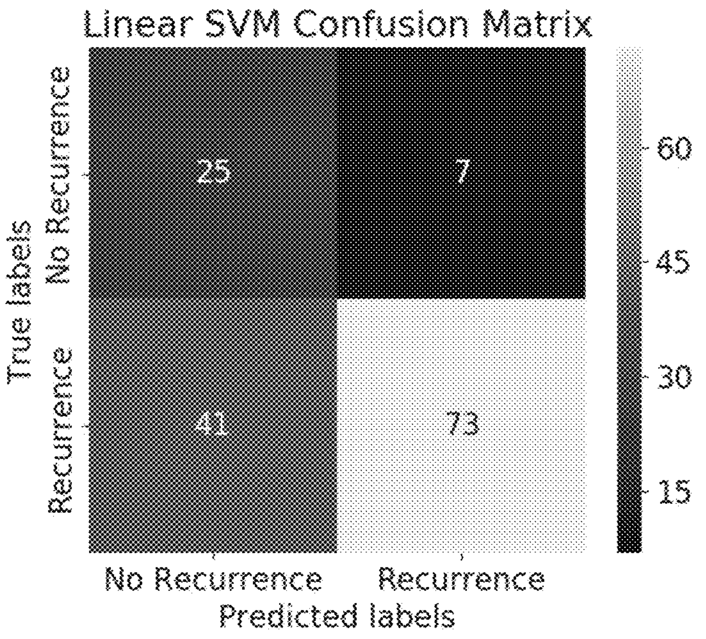
FIG. 14 Confusion matrix for the predictive algorithm
Figure 15:
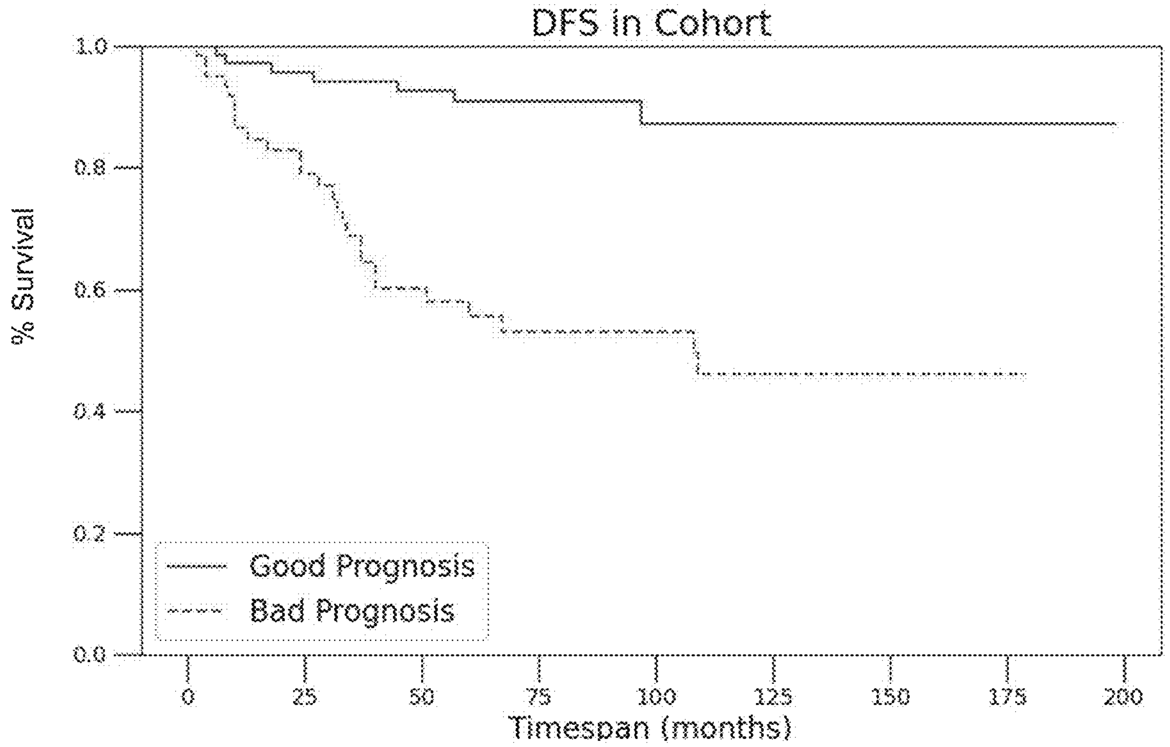
FIG. 15 Shows Kaplan Meier curves of disease free survival based on an algorithm using CLU, DPT and TTV values, for the total population of the cohort.
Figure 16:
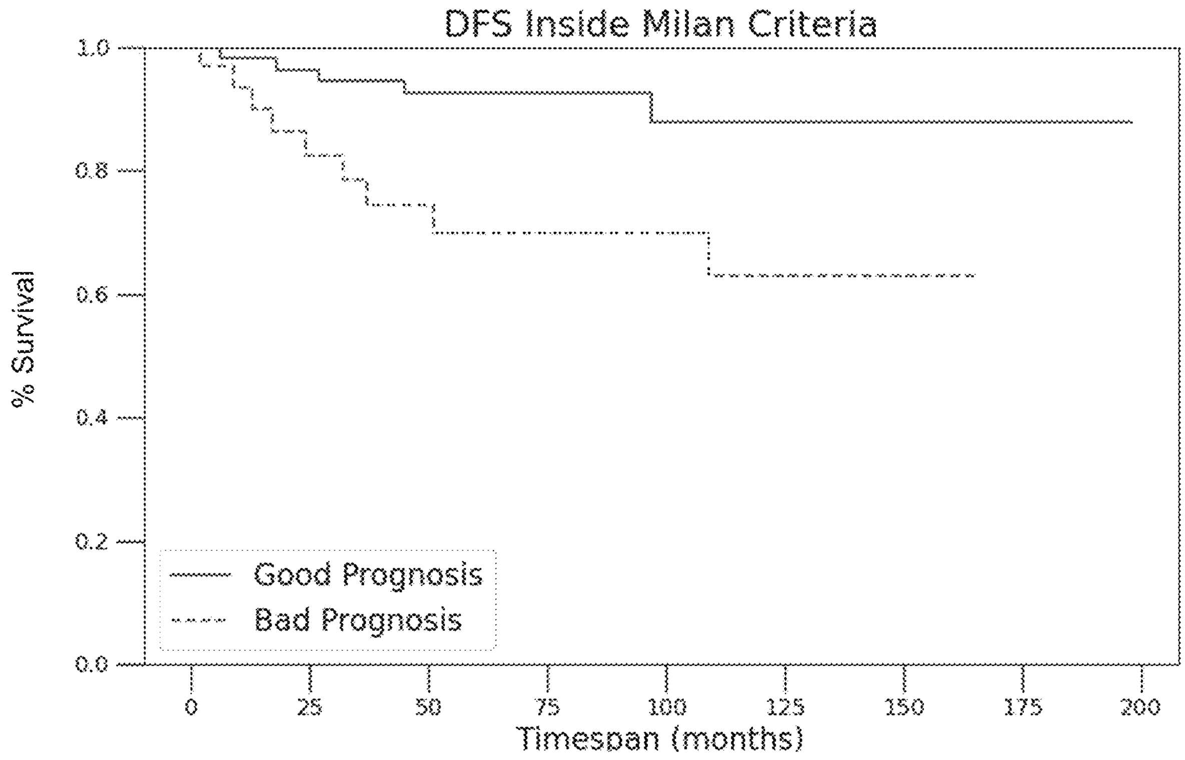
FIG. 16 Shows Kaplan Meier curves of disease free survival based on an algorithm using CLU, DPT and TTV values, for patients outside Milan criteria FIG. 17 Shows Kaplan Meier curves of disease free survival based on an algorithm using CLU, DPT and TTV values, for patients inside Milan criteria
Figure 17:
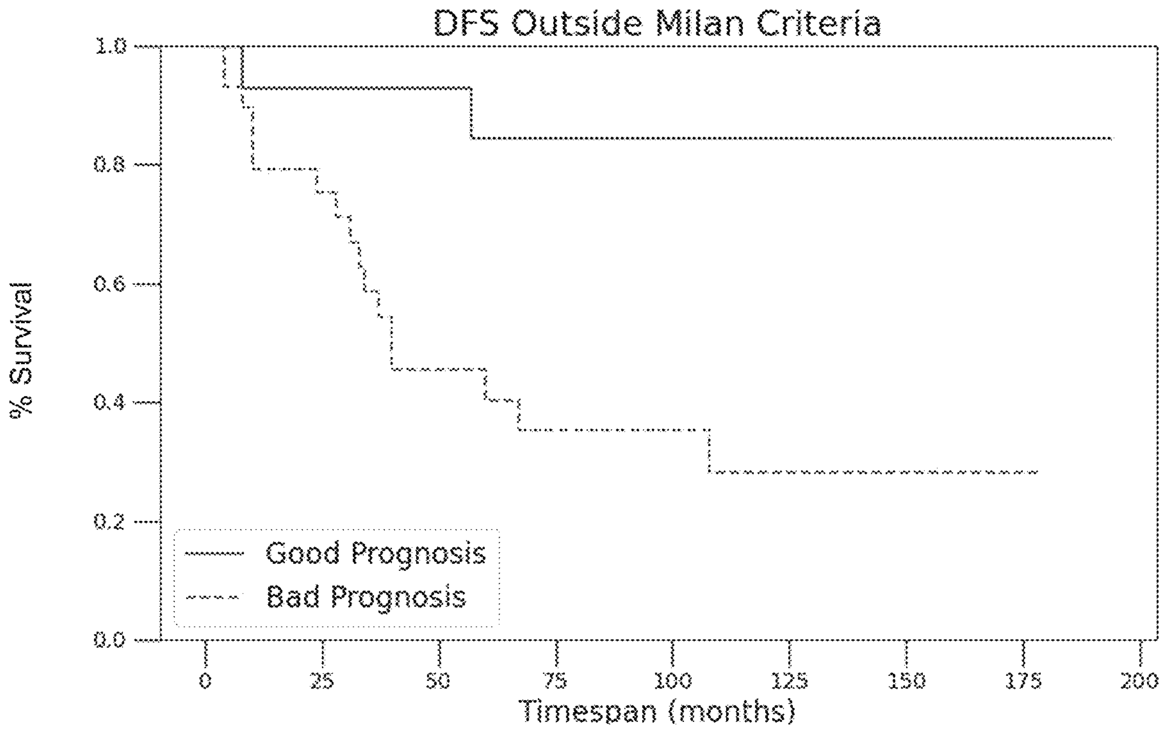

The cohort comprised of 154 patients was assessed with the multivariate algorithm with three variables. Variables were binarized using a thresholding technique where patients below the threshold were assigned a 0 value for that feature and patients above the threshold were assigned a value of 1. Units for the threshold are the same as the respective feature (ΔCt for gene expression and volume units for tumor volume). The used threshold values were −0.54 ΔCt for CLU, 7 ΔCt for DPT, and 115 $cm^3$ for TTV. The following results were obtained after the evaluation procedure, demonstrating an algorithm incorporating binary data from multiple indicator genes and tumour volume precisely classifies patients who are likely to exhibit disease recurrence following LT to treat HCC (accuracy 67%, false positives 22%, precision 91%, recall 64%, FIG. 14, FIG. 15). The precision rate of classification was also favourable where performed on patient subsets classified either as inside (accuracy 69%, false positives 36%, precision 92%, recall 71%, FIG. 16) or outside (accuracy 62%, false positives 11%, precision 87%, recall 45%, FIG. 17) the Milan criteria used in current clinical practice, suggesting classification of patients based on a binary score based on thresholds of indicator gene expression, and tumour volume, can identify a subset of patients with a likelihood of favourable outcome following LT that would otherwise be ruled out of receiving the procedure.

As an example, patient 1 has the following values DPT=10.48, CLU=5.34 and TTV=18.0 and patient 2 has DPT=4.39, CLU=0.84 and TTV=5.0. These values are then binarized using the respective thresholds resulting in binary values for each variable. The variables are provided to the linear kernel SVM algorithm to produce a binary value indicating a prediction of Recurrence. The model is capable of producing an estimated probability, in this example the result is itself binarized to segregate values above and below 50% probability to simplify the output. Result interpretation is simple as the output being a binary value just indicates whether the prediction is that Recurrence will occur (R, 0) or that no Recurrence is foreseeable (NR, 1) (Table. 7).

TABLE 7

Example of classification of outcome of LT using SVM algorithm for HHC patients.

| Patient | Variable | Value | Binarization | Estimated Probability | Outcome |
|---|---|---|---|---|---|
| 1 | CLU | 5.34 | 0 | 33% | 0 (R) |
| | DPT | 10.48 | 1 | | |
| | TTV | 18.0 | 0 | | |
| 2 | CLU | 0.84 | 1 | 59% | 1 (NR) |
| | DPT | 4.39 | 0 | | |
| | TTV | 5.0 | 0 | | |

Finally, the question of heterogeneity was also considered. Samples from different locations of the same tumour were available in 7 patients. The expression levels' variation was measured in relation to the housekeeping gene for CLU and DPT and whether a different value would cause migration of the group set by the cut-off values previously calculated ("group migration"). In these samples, DPT had little variation in expression levels and no patient had to migrate to another group based on these values. CLU expression, on the other hand, appeared to be associated with tumoral heterogeneity. These results suggest a higher probability of homogeneity of intra-tumoral gene expression for DPT.

CAPNS1

In a study involving 192 patients undergoing LT for HCC, CAPNS1 overexpression was significantly associated with tumour number and size, tumour encapsulation, venous invasion and pTNM stage. Multivariate analysis revealed CAPN4 expression as a powerful independent prognostic factor for survival of HCC patients (HR 4.068, C.I. 2.524-6.555; p<0.001. The inventors demonstrated association of CAPNS1 expression and recurrence (p<0.001). However, no correlation with OS or DFS was demonstrated and no cut-off value of ΔCt proved useful in discriminating patients that would or would not recur. CAPNS1 is a promising marker for combination with other discriminatory markers.

Example 6: Materials and Methods

Molecular Prognostic Biomarkers

Once clinical factors related to prognosis were identified, the inventors aimed to identify molecular biomarkers that could have greater discriminative power regarding prognosis of HCC. Due to this, a cooperative study between CHBPT of Curry Cabral Hospital and the company Ophiomics—Precision Medicine, with Professor José

Pereira Leal as the Principal Investigator, and one Co-investigators, Joana Cardoso Vaz, was established. The study of molecular biomarkers included data mining and bioinformatics analysis of public repositories of HCC patients and of published literature on biomarkers for HCC.

Data Mining and Bioinformatics Analysis

Mining and bioinformatics analysis of molecular data at public repositories from HCC patients submitted to liver resection and transplantation was performed. Available public data on HCC patients was reanalysed with the analysis pipeline of the inventors including expression-profiling data of miRNAs and mRNAs.

Prognostic Molecular Markers in Hepatocellular Carcinoma: A Systematic Review

The inventors searched the literature for previously published biomarkers on HCC patients submitted to LT. As data in LT patients is scarce and important information can be obtained in cohorts of patients submitted to liver resection, studies with biomarkers in LR were included in the analysis. A systematic literature review of the available evidence for the role of molecular biomarkers on the prognosis of patients undergoing resection or transplantation of HCC was performed. The review followed the general guidelines of the standards for systematic reviews from the Institute of Medicine of the National Academies. The objective of this review was to assess the role of molecular biomarkers in the prognosis of patients submitted to LR or LT for HCC.

Population: the search was restricted to journal articles in English Language and was conducted from January 2008 up to October 2016. Studies published in abstract form only, unpublished studies and articles published in non-peer reviewed journals were not included. Animal and in-vitro work was also excluded. Studies of molecular markers not related to prognosis of HCC were also excluded. Interventions: Liver resection and transplantation for HCC. The reason to select resection was due to the scarcity of studies on LT. Outcomes: Main outcomes searched are disease-free survival, recurrence and overall survival. Study design: as randomized controlled trials (RCTs) and controlled trials are rare in this setting, cohort studies were eligible for inclusion, even of retrospective nature, due to scarcity of data. Case series were accepted and case reports were excluded from the review. Economic evaluations were also excluded. Searches of the PubMed, Clinical key and Cochrane databases were performed using the following keywords in varied combinations: hepatocellular carcinoma, surgery, resection, transplantation, prognosis, molecular and biomarkers. Cited references in articles identified were used to find further relevant publications. Retrieved data included data type (mRNA, miRNA and protein), prognosis information, specific genes involved, good or bad prognostic genes, alteration type (overexpression, downregulation, hyper-hypomethylation and mutation), patient sample, statistical data and author's observations. Biomarkers were selected according to predictive power, number of citations amongst different centres, capacity to reproduce the technique and available reagents. After stringent selection of top biomarker candidates, a pilot study was performed.

Study Population

Inclusion and exclusion criteria were the same as previously used in the study on clinical biomarkers. Inclusion criteria: patients submitted to liver transplantation for hepatocellular carcinoma Exclusion criteria: age below 18 years; absence of cirrhosis; fibrolamellar histologic or hepatocholangiocarcinoma histologic type; absence of histological confirmation of HCC; and additionally, since the main outcome measure of the inventors was recurrence/disease-free survival, the inventors excluded cases with perioperative mortality, extra hepatic invasion and residual disease. The complete population of 301 patients submitted to LT for HCC between September 1992 and February 2014 was considered. From the 231 patients obtained after applying exclusion criteria, the inventors only included patients with more than 5 years of follow-up. The final set of samples used in the present study (pilot set and validation set) included 180 patients. Pilot Set: the pilot set included patients beyond Milan criteria with (n=6) and without recurrence (n=7) and patients within Milan criteria with early recurrence (n=6) and with no recurrence (n=7). The subset of biomarkers passing the selection criteria in the pilot study went through a second round of analysis with the validation set. Validation Set: excluding, from the initial population of 275 patients, patients previously included in the pilot set, patients with perioperative mortality, extra hepatic invasion, residual disease and less than 5 years of follow up, there were 154 patients initially included in the validation set.

Sample Collection

The 180 patients who underwent liver transplantation in the Hepato-Biliary-Pancreatic and Transplantation Centre of Hospital Curry Cabral had their tumour specimens fixed in formalin and preserved in paraffin blocks. For all selected blocks, histopathological characterization and area selection was carried out on haematoxylin- and eosin-(HE) stained sections under the supervision of an experienced pathologist. The medical ethical review committee of Hospital Curry Cabral and the ethical review board of NOVA Medical School both approved the study.

RNA Extraction and cDNA Synthesis

Archived FFPE tissue sections (5 μm) were deparaffinised and counterstained with Mayer's haematoxylin and eosin. All samples were macro dissected under the pathologist guidance. Total RNA was extracted with the RNeasy FFPE kit (Qiagen), according to manufacturer's instructions with a slight modification: proteinase K cell-lysis at 56° C. was performed overnight. The RNase-Free DNase Set (Qiagen) "on column" DNA digestion procedure was included. Each extracted RNA sample was reverse-transcribed with the SuperScript™ VILO™ cDNA Synthesis Kit (Thermo Fisher Scientific).

TABLE 6

Primer sequences for target and reference genes.

Target genes

| Symbol | Forward primer | SEQ ID | Reverse primer | SEQ ID | Amp. ength |
|---|---|---|---|---|---|
| OSGIN | CTGGAAGCACCGGAAGGAG | 1 | CCTTCGATGGAGTGCCAGG | 17 | 84 |
| ADAMTS5 | CCATATGTTCTCCAGAGCGCAG | 2 | GTAAATGTCCGATTTCGTGAGCC | 18 | 90 |

TABLE 6-continued

| Primer sequences for target and reference genes. | | | | | |
|---|---|---|---|---|---|
| EYA4 | ATTCCAGGTCTATGGAAATGCAGG | 3 | CAGTTTGGAGCTACCTGGAGTAT | 19 | 83 |
| MUC15 | CGTCAGATCCCCAAAAAGAAAAT | 4 | AAGTAGCCCACAAGAGTAAGCA | 20 | 100 |
| FBXW7 | GCAACAACGACGCCGAAT | 5 | GTCCACTCCAGCTCTGAAAC | 21 | 83 |
| SPRY2 | CCGCGATCACGGAGTTCA | 6 | CCACTCTGAGCTCTGGCCT | 22 | 85 |
| DPT | AACTACGCCTGCATGCC | 7 | GCACGTCTGGTACCATTCCA | 23 | 99 |
| NOTCH1 | CTACGTGCCCTGCAGCC | 8 | CCGGTGAAGCCTGGCA | 24 | 99 |
| CCR6 | GCCTGTGAGCTGAAGGGG | 9 | CATTGATTCCCCGCTTCATTGTG | 25 | 88 |
| CLU | ACTCTGCTGCTGTTTGTGGG | 10 | TGGACATTTCCTGGAGCTCATT | 26 | 97 |
| SALL4 | GACTCACACACTGGAGAGAAGCC | 11 | CATGTAGTGAACCTTTAAGTTGC | 27 | 85 |
| CAPNS1 | GTTGTGACACGACACCCTGA | 12 | ATCCATCACGGCCACCA | 28 | 78 |
| CD24 | GGGACATGGGCAGAGCAATG | 13 | ATAAATCTGCGTGGGTAGGAGC | 29 | 80 |
| DKK1 | CACCCAGGCTCTGCAGTC | 14 | GGGTACGGCTGGTAGTTGTC | 30 | 89 |
| HNF1B | GATGCTCAGTGAGGACCCTTG | 15 | GGTGACATCGACCACCTCC | 31 | 94 |
| SLC16A4 | CCTACCTTTCACCTGGTAGCC | 16 | GTCTCAAGGATACCTGCTACAGAA | 32 | 92 |
| Reference genes | | | | | |
| Symbol | Forward primer | SEQ ID NO | Forward primer | SEQ ID NO | Amp. ength |
| RPL13A | CGTGCGAGGTATGCTGCCCC | 33 | GGCGGTGGGATGCCGTCAAA | 34 | 84 |

Quantitative Real-Time PCR

RNA concentration and integrity could not be assessed using standard methods due to known FFPE degradation issues and to the small amounts of extracted samples thus, the inventors have accessed the quantity and quality of the isolated RNA samples on an Agilent 2200 TapeStation system (Agilent) using the High Sensitivity RNA ScreenTape (Agilent). Primer sets were designed with the NCBI Primer-BLAST tool (Ye et al., BMC Bioinformatics 2012; 13:134), to work at 60° C. and with an amplicon length of 70-100 bp (table 6) and were purchased from Invitrogen (Thermo Fisher Scientific). Duplicates of each sample were analysed by RT-qPCR using SsoFast™ EvaGreen® Supermix (Bio-Rad, Hercules CA, USA) reagent in 10 µL of reaction mixture containing template (1 µL, 0.5-1 ng/µL) and primers (0.5 µM each). Samples were processed in a CFX96 Touch™ Real-Time PCR Detection System (Bio-Rad, Hercules CA, USA) according to the cycling program: 98° C. for 120 s, 50 cycles of 98° C. for 5s and 60° C. for 15s. Fluorescence data collection occurred at 60° C. Data and Statistical Analysis. Relative differential expression analysis of target genes by RT-qPCR was based on the 2-ΔΔCt, or ΔCt methodology to calculate the fold change in expression, wherein values above 1 indicate upregulation and below 1 are downregulated, from Livak et al., Methods 2001; 25(4):402-8 using mean quantification cycle of duplicates as cycle threshold (Ct) compared to the Ct of the calibrator gene ribosomal protein L13a (RPL13A). The differential expression of target genes using the RT-qPCR data between the set of samples with disease recurrence (R) and without (nonR) was performed with R language for Statistical Computing (Team RDC, Austria, 2009) and the statistical significance calculated with Wilcoxon Rank Sum test (confidence level=0.95).

Further, the obtained RT-qPCR data was also correlated separately for each candidate target gene with patients' disease-free survival using the same methodology as previously described for the clinical markers. Continuous variables were presented as medians with the interquartile range (IQR) or means and standard deviation (SD) and compared using an independent samples t-test. Demographic variables of interest in transplant patients were compared using Student's t test, Pearson's chi square test or Fisher's exact test as appropriate. The outcome variables were recurrence (disease-free survival) and death (overall survival). Time to outcome was calculated using the date of transplantation until the date of the event or the date of last follow-up period for patients who did not experience the event. Kaplan-Meier survival curves were constructed for outcome analysis after transplantation. The effect of demographic variables on disease-free and overall survival was examined using the log-rank test and Cox regression model. Cut-off values were determined by receiver operating characteristics (ROC) analysis. For multivariate analysis, all variables significant to $P<0.20$ for the outcome were included in a Cox proportional hazards model (Therneau et al., Springer-Verlag, 2000) or in a multiple logistic regression model depending on the type of outcome. Backward selection was performed to retain significant variables. Separate stratified survival analyses were performed as judged necessary. P values less than 0.05 were considered significant. Statistical analysis was performed using SPSS versions 22.0 and 24.0 (SPSS Inc., Chicago, IL). The linear kernel SVM algorithm was developed in a Python 3.6.7 environment using the following packages for data manipulation and classification: scikit-learn (0.23.2); numpy (1.19.1); pandas (0.23.4).

We claim:

1. A method for treating hepatocellular carcinoma (HCC) in a patient, comprising:

determining whether a patient previously diagnosed with HCC is likely to have an increased chance of disease-free survival (DFS) at 5 and 10 years following liver transplantation, by:

detecting, in a liver sample obtained from the patient, overexpression of each gene of a group of indicator genes comprising clusterin (CLU) and dermatopontin (DPT);

wherein overexpression of both genes of the group of indicator genes indicates that the patient will have a greater chance of disease-free survival (DFS) at 5 and 10 years following liver transplantation than a patient in which only one of CLU or DPT is overexpressed; and performing liver transplantation on the patient determined to have an increased chance of DFS at 5 and 10 years.

2. The method of claim 1, wherein the group of indicator genes further comprises at least one of:

calpain small subunit 1 (CAPNS1),

F-box and WD repeat containing protein 7 (FBXW7); or

Sprouty RTK signalling antagonist 2 (SPRY2).

3. The method of claim 1, wherein overexpression of each gene of the group of indicator genes is in relation to a threshold.

4. The method of claim 1, wherein determining whether a patient previously diagnosed with HCC is likely to have a an increased chance of DFS at 5 and 10 years further comprises, measuring total tumor volume in the patient, and wherein overexpression of DPT and CLU, and a total tumour volume of $\leq$115 $cm^3$ are indicative of an increased chance of DFS at 5 and 10 years.

5. The method of claim 3, wherein detecting overexpression of each gene of a group of indicator genes is determined by polymerase chain reaction, and wherein said indicator gene expression value relative to said threshold is determined as a difference of a threshold cycle number of said indicator gene and a threshold cycle number of an internal control gene, wherein said threshold cycle number is a PCR cycle number at which a product of said indicator gene and said internal control gene are is detected.

6. The method of claim 5, wherein an indicator gene is said to be overexpressed if the difference of the threshold cycle number of the indicator gene DPT is higher than 7, and the difference of the threshold cycle number of the indicator gene CLU is higher than-0.54.

7. The method of claim 4, wherein the overexpression of the indicator genes in a patient sample, and/or the tumour volume measurement is incorporated into an algorithm to provide a value reflecting the likelihood of disease recurrence, and wherein a lower likelihood of disease recurrence indicates an increased chance of DFS at 5 and 10 years.

8. The method of claim 7, wherein the algorithm is a support vector machine algorithm.

9. The method of claim 7, wherein the algorithm is a linear kernel support vector machine algorithm.

10. The method of claim 1, wherein the chance of DFS at 5 and 10 years following liver transplantation is determined to be 78% and 60%, respectively.

* * * * *

SEQUENCE LISTING

<160> NUMBER OF SEQ ID NOS: 34

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
ctggaagcac cggaaggag 19

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
ccatatgttc tccagagcgc ag 22

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
attccaggtc tatggaaatg cagg 24

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
cgtcagatcc ccaaaaagaa aat 23

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
gcaacaacga cgccgaat 18

<210> SEQ ID NO 6
<211> LENGTH: 18
<212> TYPE: DNA
<213> ORGANISM: Artificial Sequence
<220> FEATURE:
<223> OTHER INFORMATION: Sythetic oligonucleotide

<400> SEQUENCE: 6
ccgcgatcac ggagttca 18

<210> SEQ ID NO 7
<211> LENGTH: 17
<212> TYPE: DNA
<213> ORGANISM: Artificial Sequence
<220> FEATURE:
<223> OTHER INFORMATION: Sythetic oligonucleotide

<400> SEQUENCE: 7
aactacgcct gcatgcc 17

<210> SEQ ID NO 8
<211> LENGTH: 17
<212> TYPE: DNA
<213> ORGANISM: Artificial Sequence
<220> FEATURE:
<223> OTHER INFORMATION: Sythetic oligonucleotide

<400> SEQUENCE: 8
ctacgtgccc tgcagcc 17

<210> SEQ ID NO 9
<211> LENGTH: 18
<212> TYPE: DNA
<213> ORGANISM: Artificial Sequence
<220> FEATURE:
<223> OTHER INFORMATION: Sythetic oligonucleotide

<400> SEQUENCE: 9
gcctgtgagc tgaagggg 18

<210> SEQ ID NO 10
<211> LENGTH: 20
<212> TYPE: DNA
<213> ORGANISM: Artificial Sequence
<220> FEATURE:
<223> OTHER INFORMATION: Sythetic oligonucleotide

<400> SEQUENCE: 10
actctgctgc tgtttgtggg 20

<210> SEQ ID NO 11
<211> LENGTH: 23
<212> TYPE: DNA
<213> ORGANISM: Artificial Sequence
<220> FEATURE:
<223> OTHER INFORMATION: Sythetic oligonucleotide

<400> SEQUENCE: 11
gactcacaca ctggagagaa gcc 23

<210> SEQ ID NO 12
<211> LENGTH: 20
<212> TYPE: DNA
<213> ORGANISM: Artificial Sequence
<220> FEATURE:
<223> OTHER INFORMATION: Sythetic oligonucleotide

<400> SEQUENCE: 12
gttgtgacac gacaccctga 20

<210> SEQ ID NO 13
<211> LENGTH: 20
<212> TYPE: DNA
<213> ORGANISM: Artificial Sequence
<220> FEATURE:
<223> OTHER INFORMATION: Sythetic oligonucleotide

<400> SEQUENCE: 13
gggacatggg cagagcaatg 20

<210> SEQ ID NO 14
<211> LENGTH: 18
<212> TYPE: DNA
<213> ORGANISM: Artificial Sequence
<220> FEATURE:
<223> OTHER INFORMATION: Sythetic oligonucleotide

<400> SEQUENCE: 14
cacccaggct ctgcagtc 18

<210> SEQ ID NO 15
<211> LENGTH: 21
<212> TYPE: DNA
<213> ORGANISM: Artificial Sequence
<220> FEATURE:
<223> OTHER INFORMATION: Sythetic oligonucleotide

<400> SEQUENCE: 15
gatgctcagt gaggaccctt g 21

<210> SEQ ID NO 16
<211> LENGTH: 21
<212> TYPE: DNA
<213> ORGANISM: Artificial Sequence
<220> FEATURE:
<223> OTHER INFORMATION: Sythetic oligonucleotide

<400> SEQUENCE: 16
cctacctttc acctggtagc c 21

<210> SEQ ID NO 17
<211> LENGTH: 19
<212> TYPE: DNA
<213> ORGANISM: Artificial Sequence
<220> FEATURE:
<223> OTHER INFORMATION: Sythetic oligonucleotide

<400> SEQUENCE: 17
ccttcgatgg agtgccagg 19

<210> SEQ ID NO 18
<211> LENGTH: 23
<212> TYPE: DNA
<213> ORGANISM: Artificial Sequence
<220> FEATURE:
<223> OTHER INFORMATION: Sythetic oligonucleotide

<400> SEQUENCE: 18
gtaaatgtcc gatttcgtga gcc 23

<210> SEQ ID NO 19
<211> LENGTH: 23
<212> TYPE: DNA
<213> ORGANISM: Artificial Sequence
<220> FEATURE:
<223> OTHER INFORMATION: Sythetic oligonucleotide

<400> SEQUENCE: 19
cagtttggag ctacctggag tat 23

<210> SEQ ID NO 20
<211> LENGTH: 22
<212> TYPE: DNA
<213> ORGANISM: Artificial Sequence
<220> FEATURE:
<223> OTHER INFORMATION: Sythetic oligonucleotide

<400> SEQUENCE: 20
aagtagccca caagagtaag ca 22

<210> SEQ ID NO 21
<211> LENGTH: 20
<212> TYPE: DNA
<213> ORGANISM: Artificial Sequence
<220> FEATURE:
<223> OTHER INFORMATION: Sythetic oligonucleotide

<400> SEQUENCE: 21
gtccactcca gctctgaaac 20

<210> SEQ ID NO 22
<211> LENGTH: 19
<212> TYPE: DNA
<213> ORGANISM: Artificial Sequence
<220> FEATURE:
<223> OTHER INFORMATION: Sythetic oligonucleotide

<400> SEQUENCE: 22
ccactctgag ctctggcct 19

<210> SEQ ID NO 23
<211> LENGTH: 20
<212> TYPE: DNA
<213> ORGANISM: Artificial Sequence
<220> FEATURE:
<223> OTHER INFORMATION: Sythetic oligonucleotide

<400> SEQUENCE: 23
gcacgtctgg taccattcca 20

<210> SEQ ID NO 24
<211> LENGTH: 16
<212> TYPE: DNA
<213> ORGANISM: Artificial Sequence
<220> FEATURE:
<223> OTHER INFORMATION: Sythetic oligonucleotide

<400> SEQUENCE: 24
ccggtgaagc ctggca 16

<210> SEQ ID NO 25
<211> LENGTH: 23
<212> TYPE: DNA
<213> ORGANISM: Artificial Sequence
<220> FEATURE:
<223> OTHER INFORMATION: Sythetic oligonucleotide

<400> SEQUENCE: 25
cattgattcc ccgcttcatt gtg 23

<210> SEQ ID NO 26
<211> LENGTH: 22
<212> TYPE: DNA
<213> ORGANISM: Artificial Sequence
<220> FEATURE:
<223> OTHER INFORMATION: Sythetic oligonucleotide

<400> SEQUENCE: 26
tggacatttc ctggagctca tt 22

<210> SEQ ID NO 27

<211> LENGTH: 23
<212> TYPE: DNA
<213> ORGANISM: Artificial Sequence
<220> FEATURE:
<223> OTHER INFORMATION: Sythetic oligonucleotide

<400> SEQUENCE: 27
catgtagtga acctttaagt tgc 23

<210> SEQ ID NO 28
<211> LENGTH: 17
<212> TYPE: DNA
<213> ORGANISM: Artificial Sequence
<220> FEATURE:
<223> OTHER INFORMATION: Sythetic oligonucleotide

<400> SEQUENCE: 28
atccatcacg gccacca 17

<210> SEQ ID NO 29
<211> LENGTH: 22
<212> TYPE: DNA
<213> ORGANISM: Artificial Sequence
<220> FEATURE:
<223> OTHER INFORMATION: Sythetic oligonucleotide

<400> SEQUENCE: 29
ataaatctgc gtgggtagga gc 22

<210> SEQ ID NO 30
<211> LENGTH: 20
<212> TYPE: DNA
<213> ORGANISM: Artificial Sequence
<220> FEATURE:
<223> OTHER INFORMATION: Sythetic oligonucleotide

<400> SEQUENCE: 30
gggtacggct ggtagttgtc 20

<210> SEQ ID NO 31
<211> LENGTH: 19
<212> TYPE: DNA
<213> ORGANISM: Artificial Sequence
<220> FEATURE:
<223> OTHER INFORMATION: Sythetic oligonucleotide

<400> SEQUENCE: 31
ggtgacatcg accacctcc 19

<210> SEQ ID NO 32
<211> LENGTH: 24
<212> TYPE: DNA
<213> ORGANISM: Artificial Sequence
<220> FEATURE:
<223> OTHER INFORMATION: Sythetic oligonucleotide

<400> SEQUENCE: 32
gtctcaagga tacctgctac agaa 24

<210> SEQ ID NO 33
<211> LENGTH: 20
<212> TYPE: DNA
<213> ORGANISM: Artificial Sequence
<220> FEATURE:
<223> OTHER INFORMATION: Sythetic oligonucleotide

<400> SEQUENCE: 33

-continued

```
cgtgcgaggt atgctgcccc                                                    20


<210> SEQ ID NO 34
<211> LENGTH: 20
<212> TYPE: DNA
<213> ORGANISM: Artificial Sequence
<220> FEATURE:
<223> OTHER INFORMATION: Sythetic oligonucleotide

<400> SEQUENCE: 34

ggcggtggga tgccgtcaaa                                                    20
```